(12) United States Patent
Luk et al.

(10) Patent No.: US 6,197,804 B1
(45) Date of Patent: Mar. 6, 2001

(54) 4,5-AZOLO-OXINDOLES

(75) Inventors: Kin-Chun Luk, North Caldwell; Steven Gregory Mischke, Florham Park, both of NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 09/571,541

(22) Filed: May 16, 2000

Related U.S. Application Data

(62) Division of application No. 09/464,507, filed on Dec. 15, 1999.
(60) Provisional application No. 60/112,611, filed on Dec. 17, 1998, and provisional application No. 60/149,055, filed on Jun. 16, 1999.

(51) Int. Cl.[7] .................. A61K 31/424; A61K 31/429; C07D 513/04; C07D 498/04
(52) U.S. Cl. ............... 514/366; 514/322; 514/375; 514/388; 514/393; 546/199; 548/151; 548/218; 548/302.1
(58) Field of Search .................. 548/302.1, 218, 548/151; 546/199; 514/322, 388, 393, 366, 375

(56) References Cited

U.S. PATENT DOCUMENTS

| | | | |
|---|---|---|---|
| 4,556,672 | 12/1985 | Kadin | 514/414 |
| 4,730,003 | * 3/1988 | Von Der Saal et al. | 514/397 |
| 5,206,261 | 4/1993 | Kawaguchi et al. | 514/418 |
| 5,322,950 | 6/1994 | Sircar et al. | 548/253 |
| 5,374,652 | 12/1994 | Buzzetti et al. | 514/418 |
| 5,397,787 | 3/1995 | Buzzetti et al. | 514/300 |
| 5,409,949 | 4/1995 | Buzzetti et al. | 514/414 |
| 5,488,057 | 1/1996 | Buzzetti et al. | 514/312 |
| 5,576,330 | 11/1996 | Buzzetti et al. | 514/307 |
| 5,792,783 | 8/1998 | Tang et al. | 514/397 |
| 5,834,504 | 11/1998 | Tang et al. | 514/418 |
| 5,883,113 | 3/1999 | Tang et al. | 514/418 |
| 5,883,116 | 3/1999 | Tang et al. | 514/418 |
| 5,886,020 | 3/1999 | Tang et al. | 514/418 |

FOREIGN PATENT DOCUMENTS

| | | |
|---|---|---|
| 0436333 A2 | 12/1990 | (EP) . |
| 0580502 A1 | 7/1993 | (EP) . |
| WO 92/07830 | 5/1992 | (WO) . |
| WO 95/01349 | 1/1995 | (WO) . |
| WO 96/00226 | 1/1996 | (WO) . |
| WO 96/16964 | 6/1996 | (WO) . |
| WO 96/22976 | 8/1996 | (WO) . |
| WO 96/32380 | 10/1996 | (WO) . |
| WO 96/40116 | 12/1996 | (WO) . |
| WO 97/11692 | 4/1997 | (WO) . |
| WO 97/16447 | 5/1997 | (WO) . |
| WO 97/45409 | 12/1997 | (WO) . |
| WO 97/46551 | 12/1997 | (WO) . |
| WO 98/07695 | 2/1998 | (WO) . |
| WO 98/24432 | 6/1998 | (WO) . |
| WO 98/50356 | 11/1998 | (WO) . |
| WO 99/10325 | 3/1999 | (WO) . |
| WO 99/15500 | 4/1999 | (WO) . |
| WO 99/48868 | 9/1999 | (WO) . |
| WO 99/61422 | 12/1999 | (WO) . |
| WO 00 08202 | 2/2000 | (WO) . |
| WO 00/12084 | 3/2000 | (WO) . |

OTHER PUBLICATIONS

Abstract Acc. No. 94–028085/199404 (Abstract of EP 0580502).

Sun et al., J. Med. Chem., 41:2588–2603 (1998).

Sun et al., "Synthesis and Biological Evaluation of Novel 3–[(Substituted pyrrol–2–yl) methylidenyl] indolin–2–ones as Potent and Selective Inhibitors of the FlK–1/KDR Receptor Tyrosine Kinase", Abstract presented as Trip Report: ACS National Meeting, Dallas, Texas, Apr. 1998.

* cited by examiner

*Primary Examiner*—Laura L. Stockton
(74) *Attorney, Agent, or Firm*—George W. Johnston; Patricia S. Rocha-Tramaloni

(57) ABSTRACT

Disclosed are novel 4,5-azolo-oxindoles having the formula

I

These compounds inhibit cyclin-dependent kinases (CDKs), in particular CDK2. Thus, these compounds and their pharmaceutically acceptable salts, and *prodrugs of said compounds, are anti-proliferative agents useful in the treatment or control of cell proliferative disorders, in particular cancer. Also disclosed are pharmaceutical compositions containing these compounds, and methods for the treatment and/or prevention of cancer, particularly in the treatment or control of solid tumors using these compounds, as well as intermediates useful in the preparation of compounds of formula I.

17 Claims, No Drawings

4,5-AZOLO-OXINDOLES

CROSS REFERENCE TO RELATED APPLICATION

This is a divisional of copending application(s) Ser. No. 09/464,507 filed on Dec. 15, 1999 which claims the benefit of Ser. No. 60/112,611 filed Dec. 17, 1998 and claims benefit of Ser. No. 60/149,055 filed Aug. 16, 1999.

FIELD OF THE INVENTION

The present invention is directed to novel 4,5-azolo-oxindoles which inhibit cyclin-dependent kinases (CDKs), in particular CDK2. These compounds and their pharmaceutically acceptable salts, and prodrugs of said compounds, are anti-proliferative agents useful in the treatment or control of cell proliferative disorders, in particular cancer. The invention is also directed to pharmaceutical compositions containing such compounds, and to methods for the treatment and/or prevention of cancer, particularly in the treatment or control of solid tumors. The compounds of the invention are especially useful in the treatment or control of breast and colon tumors.

BACKGROUND OF THE INVENTION

Uncontrolled cell proliferation is the hallmark of cancer. Cancerous tumor cells typically have some form of damage to the genes that directly or indirectly regulate the cell-division cycle.

Cyclin-dependent kinases (CDKs) are enzymes which are critical to cell cycle control. See, e.g., Coleman et al., "Chemical Inhibitors of Cyclin-dependent Kinases," *Annual Reports in Medicinal Chemistry*, vol. 32, 1997, pp. 171–179. These enzymes regulate the transitions between the different phases of the cell cycle, such as the progression from the $G_1$ phase to the S phase (the period of active DNA synthesis), or the progression from the $G_2$ phase to the M phase, in which active mitosis and cell-division occurs. See, e.g., the articles on this subject appearing in *Science*, vol. 274, Dec. 6, 1996, pp. 1643–1677.

CDKs are composed of a catalytic CDK subunit and a regulatory cyclin subunit. The cyclin subunit is the key regulator of CDK activity, with each CDK interacting with a specific subset of cyclins: e.g. cyclin A (CDK1, CDK 2). The different kinase/cyclin pairs regulate progression through specific stages of the cell cycle. See, e.g., Coleman, supra.

Aberrations in the cell cycle control system have been implicated in the uncontrolled growth of cancerous cells. See, e.g., Kamb, "Cell-Cycle Regulators and Cancer," *Trends in Genetics*, vol. 11, 1995, pp. 136–140; and Coleman, supra. In addition, changes in the expression of or in the genes encoding CDK's or their regulators have been observed in a number of tumors. See, e.g., Webster, "The Therapeutic Potential of Targeting the Cell Cycle," *Exp. Opin. Invest. Drugs*, Vol. 7, pp. 865–887 (1998), and references cited therein. Thus, there is an extensive body of literature validating the use of compounds inhibiting CDKs as anti-proliferative therapeutic agents. See, e.g. U.S. Pat. No. 5,621,082 to Xiong et al; EP 0 666 270 A2; WO 97/16447; and the references cited in Coleman, supra, in particular reference no. 10. Thus, it is desirable to identify chemical inhibitors of CDK kinase activity.

It is particularly desirable to identify small molecule compounds that may be readily synthesized and are effective in inhibiting one or more CDKs or CDK/cyclin complexes, for treating one or more types of tumors.

Indolinone (also known as oxindole) compounds asserted to be useful in the regulating abnormal cell proliferation through tyrosine kinase inhibition are disclosed in WO 96/40116, WO 98/07695, WO 95/01349, WO 96/32380, WO 96/22976, WO 96/16964 (tyrosine kinase inhibitors), and WO 98/50356 (2-indolinone derivatives as modulators of protein kinase activity). Oxindole derivatives have also been described for various other therapeutic uses: U.S. Pat. No. 5,206,261 (improvement of cerebral function); WO 92/07830 (peptide antagonists); EP 580 502 A1 (antioxidants).

There continues to be a need for easily synthesized, small molecule compounds for the treatment of one or more types of tumors, in particular through regulation of CDKs. It is thus an object of this invention to provide such compounds and compositions containing such compounds.

SUMMARY OF THE INVENTION

The present invention relates to 4,5-azolo-oxindoles capable of inhibiting the activity of one or more CDKs, in particular CDK2. Such compounds are useful for the treatment of cancer, in particular solid tumors. In particular the compounds of the present invention are especially useful in the treatment or control of breast and colon tumors.

The compounds of the present invention are 4,5-azolo-oxindoles having the following formula:

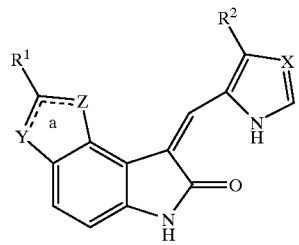

I and prodrugs and pharmaceutically active metabolites of compounds of formula I; and the pharmaceutically acceptable salts of the foregoing compounds, wherein $R^1$ is selected from the group consisting of
—H,
—OR$^3$,
—COR$^3$,
—COOR$^3$,
—CONR$^4$R$^5$,
—NR$^4$R$^5$,
lower alkyl which optionally may be substituted by the group consisting of —OR$^3$, —NR$^4$R$^5$, halogen, —COR$^3$, —COOR$^3$, —OCOR$^3$, —CONR$^4$R$^5$, —CN, —SO$_2$R$^3$, —SO$_2$NR$^4$R$^5$, cycloalkyl, heterocycle, aryl, and heteroaryl, wherein the cycloalkyl and heterocycle each may be optionally substituted by the group R$^{11}$ and the aryl and heteroaryl each may be optionally substituted by the group R$^{12}$,
cycloalkyl which optionally may be substituted by the group consisting of —OR$^3$, —NR$^4$R$^5$, halogen, —COR$^3$, —COOR$^3$, —OCOR$^3$, —CONR$^4$R$^5$, —CN —SO$_2$R$^3$,
—SO$_2$NR$^4$R$^5$, lower alkyl, heterocycle, aryt, and heteroaryt, wherein the lower alkyl and heterocycle each may be optionally substituted by the group R$^{11}$ and the aryl and heteroaryl each may be optionally substituted by the group R$^{12}$, heterocycle which optionally may be substituted by the group consisting of —$OR^3$, —$NR^4R^5$, halogen, —$COR^3$, —$COOR^3$, —$OCOR^3$, —$CONR^4R^5$ —CN, —$SO_2R^3$, —$SO_2NR^4R^5$, lower alkyl, cycloalkyl, aryl, and heteroaryl, wherein the lower alkyl and cycloalkyl each may be optionally substituted by the group $R^{11}$ and the aryl and heteroaryl each may be optionally substituted by the group $R^{12}$, aryl which optionally may be substituted by the group consisting of —$OR^3$, —$NR^4R^5$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, heteroaryl which optionally may be substituted by the group consisting of —$OR^3$, —$NR^4R^5$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, lower alkyl, cycloalkyl, heterocycle, aryl, and heteroaryl and wherein the lower alkyl, cycloalkyl and heterocycle each may be optionally substituted by the group $R^{11}$ and the aryl and heteroaryl each may be optionally substituted by the group $R^{12}$, $R^2$ is selected from the group consisting of
—H,
—$OR^3$,
—$COR^3$,
—$COOR^3$,
—$OCOR^3$,
—$CONR^4R^5$,
halogen,
—CN,
perfluoroalkyl,
—$NR^4R^5$, and
lower alkyl which optionally may be substituted by the group consisting of —$OR^3$, —$OCOR^3$, and —$NR^4R^5$;

$R^3$ is selected from the group consisting of
—H,
lower alkyl which optionally may be substituted by the group consisting of —$R^7$, —$COOR^6$, —$COR^6$, —$CONR^4R^5$, —$NR^4R^5$, —$SO_2R^6$, —$SO_2NR^4R^5$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$, heterocycle which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$, aryl which optionally may be substituted by the group consisting of —$OR^7$, —$COOR^6$, —$COR^6$, —$CONR^4R^5$, —$NR^4R^5$, $NO_2$, halogen, perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and heteroaryl which optionally may be substituted by the group consisting of —$OR^7$, —$COOR^6$, —$COR^6$, —$CONR^4R^5$, —$NR^4R^5$, $NO_2$, halogen, perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^4$ and $R^5$ are each independently selected from the group consisting of
—H,
—$COR^6$,
—$COOR^6$,
—$CONR^6R^8$, and
lower alkyl which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$, heterocycle which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, aryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and heteroaryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$; or alternatively, —$NR^4R^5$ can optionally form a ring having 3 to 7 atoms, said ring optionally including one or more additional hetero atoms and being optionally substituted by the group consisting of lower alkyl, —OR$^7$, —COR$^6$, —COOR$^6$, —CONR$^6$R$^8$, and —NR$^7$R$^8$;

R$^6$ is selected from the group consisting of
—H, and
lower alkyl which optionally may be substituted by the group consisting of cycloalkyl, heterocycle, aryl, heteroaryl, —OR$^8$, and —NR$^7$R$^8$;

R$^7$ is selected from the group consisting of
—H,
—COR$^8$,
—CONR$^9$R$^8$, and
lower alkyl which optionally may be substituted by R$^{11}$;

R$^8$ and R$^9$ are each independently selected from the group consisting of —H and lower alkyl;

R$^{11}$ is selected from the group consisting of —OR$^8$, —COR$^8$, —COOR$^8$, —OCOR$^8$, —CONR$^8$R$^9$, —NR$^8$R$^9$, —N(COR$^8$)R$^9$, —SO$_2$R$^8$, —SO$_2$NR$^8$R$^9$;

R$^{12}$ is selected from the group consisting of —OR$^8$, —COR$^8$, —COOR$^8$, —OCOR$^8$, —CONR$^8$R$^9$, —NR$^8$R$^9$, —N(COR$^8$)R$^9$, —SO$_2$R$^8$, —SO$_2$NR$^8$R$^9$, halogen, —CN, —NO$_2$, perfluoroalkyl;

X is selected from the group consisting of

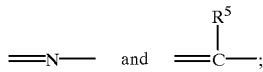

Y and Z are each independently selected from the group consisting of N, O, and S; provided that at least one of Y and Z is N; and provided further that if both Y and Z are N, then one may be substituted by the group consisting of lower alkyl and lower alkyl which optionally may be substituted by the group consisting of —OR$^7$, —NR$^4$R$^5$, cycloalkyl, heterocycle, aryl, and heteroaryl; and a is a double bond either between Y—C or Z—C.

The present invention is further directed to pharmaceutical compositions comprising a pharmaceutically effective amount of any one or more of the above-described compounds and a pharmaceutically acceptable carrier or excipient.

The present invention is also directed to novel compounds useful in the synthesis of the above described compounds.

The present invention is also directed to a method for treating solid tumors, in particular breast or colon tumors, by administering to a human patient in need of such therapy an effective amount of a compound of formula I, its salts and/or prodrugs.

DETAILED DESCRIPTION OF THE INVENTION

Definitions

As used herein, the following terms shall have the following definitions.

"Aryl" means an aromatic group having 5 to 10 atoms and consisting of 1 or 2 rings. Examples of aryl groups include phenyl and 1- or 2-naphthyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of formula I, or a pharmaceutically acceptable salt, prodrug or metabolite thereof, that significantly inhibits proliferation and/or prevents differentiation of a human tumor cell, including human tumor cell lines.

"Halogen" means fluorine, chlorine, bromine or iodine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl, quinolyl, pyrrolyl, and imidazolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"IC$_{50}$" refer to the concentration of a particular 4,5-azolo-oxindole required to inhibit 50% of a specific measured activity. IC$_{50}$ can be measured, inter alia, as is described in Example 47, infra.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from potassium, sodium, ammonium, and quarternary ammonium hydroxide, such as for example tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I which is pharmaceutically acceptable and effective.

"Prodrug" refers to a compound that may be converted under physiological conditions or by solvolysis to any of the compounds of formula I or to a pharmaceutically acceptable salt of a compound of formula I. A prodrug may be inactive when administered to a subject but is converted in vivo to an active compound of formula I.

"Substituted," as in substituted alkyl means that the substitution can occur at one or more positions and, unless otherwise indicated, that the substituents are independently selected from the specified options.

The Compounds

In one embodiment, the current invention is directed to compounds having the formula:

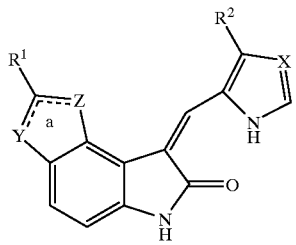

and prodrugs and pharmaceutically active metabolites of compounds of formula I, and the pharmaceutically acceptable salts of the foregoing compounds, wherein $R^1$ is selected from the group consisting of
—H,
—$OR^3$,
—$COR^3$,
—$COOR^3$,
—$CONR^4R^5$,
—$NR^4R^5$,
lower alkyl which optionally may be substituted by the group consisting of —$OR^3$, —$NR^4R^5$, halogen, —$COR^3$, —$COOR^3$, —$OCOR^3$, —$CONR^4R^5$, —CN, —$SO_2R^3$, —$SO_2NR^4R^5$, cycloalkyl, heterocycle, aryl, and heteroaryl, wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^3$, —$NR^4R^5$, halogen, —$COR^3$, —$COOR^3$, —$OCOR^3$, —$CONR^4R^5$, —CN, —$SO_2R^3$, —$SO_2NR^4R^5$, lower alkyl, heterocycle, aryl, and heteroaryl, wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^3$, —$NR^4R^5$, halogen, —$COR^3$, —$COOR^3$, —$OCOR^3$, —$CONR^4R^5$, —CN, —$SO_2R^3$, —$SO_2NR^4R^5$, lower alkyl, cycloalkyl, aryl, and heteroaryl, wherein the lower alkyl and cycloalkyl each may be optionally substituted by the group $R^{11}$ and the aryl and heteroaryl each may be optionally substituted by the group $R^{12}$,
aryl which optionally may be substituted by the group consisting of —$OR^3$, —$NR^4R^5$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$,
heteroaryl which optionally may be substituted by the group consisting of —OR, —$NR^4R$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, tower alkyl, cycloalkyl, heterocycle, aryl, and heteroaryl and wherein the lower alkyl, cycloalkyl and heterocycle each may be optionally substituted by the group $R^{11}$ and the aryl and heteroaryl each may be optionally substituted by the group $R^{12}$, $R^2$ is selected from the group consisting of
—H,
—$OR^3$,
—$COR^3$,
—$COOR^3$,
—$OCOR^3$,
$CONR^4R^5$,
halogen,
—CN,
perfluoroalkyl,
—$NR^4R^5$, and
lower alkyl which optionally may be substituted by the group consisting of —$OR^3$, —$OCOR^3$, and —$NR^4R^5$;

$R^3$ is selected from the group consisting of
—H,
lower alkyl which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$,
aryl which optionally may be substituted by the group consisting of —$OR^7$, —$COOR^6$, —$COR^6$, —$CONR^4R^5$, —$NR^4R^5$, —$NO_2$, halogen, perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^7$, —$COOR^6$, —$COR^6$, —$CONR^4R^5$, —$NR^4R^5$, —$NO_2$ halogen perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^4$ and $R^5$ are each independently selected from the group consisting of
—H,
—$COR^6$,
—$COOR^6$,
—$CONR^6R^8$, and
lower alkyl which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, lower alkyl, heterocycle, aryl, and heteroaryl, and wherein the lower alkyl, and heterocycle each may be optionally substituted by the group $R^{11}$ and the aryl and heteroaryl each may be optionally substituted by the group $R^{12}$, heterocycle which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, aryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and heteroaryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$; or alternatively, —$NR^4R^5$ can optionally form a ring having 3 to 7 atoms, said ring optionally including one or more additional hetero atoms and being optionally substituted by the group consisting of lower alkyl, —$OR^7$, —$COR^6$, —$COOR^6$, —$CONR^6R^8$, and —$NR^7R^8$;

$R^6$ is selected from the group consisting of
—H, and
lower alkyl which optionally may be substituted by the group consisting of cycloalkyl, heterocycle, aryl, heteroaryl, —$OR^8$, and —$NR^7R^8$;

$R^7$ is selected from the group consisting of
—H,
—$COR^8$,
—$CONR^9R^8$, and
lower alkyl which optionally may be substituted by $R^{11}$;

$R^8$ and $R^9$ are each independently selected from the group consisting of —H and lower alkyl;

$R^{11}$ is selected from the group consisting of —$OR^8$, —$COR^8$, —$COOR^8$, —$OCOR^8$, —$CONR^8R^9$, —$NR^8R^9$, —$N(COR^8)R^9$, —$SO_2R^8$, —$SO_2NR^8R^9$;

$R^{12}$ is selected from the group consisting of —$OR^8$, —$COR^8$, —$COOR^8$, —$OCOR^8$, —$CONR^8R^9$, —$NR^8R^9$, —$N(COR^8)R^9$, —$SO_2R^8$, —$SO_2NR^8R^9$, halogen, —CN, —$NO_2$, perfluoroalkyl;

X is selected from the group consisting of

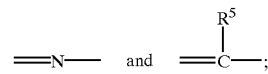

Y and Z are each independently selected from the group consisting of N, O, and S; provided that at least one of Y and Z is N; and provided further that if both Y and Z are N, then one may be substituted by the group consisting of lower alkyl and lower alkyl which is substituted by the group consisting of —$OR^7$, —$NR^4R^5$, cycloalkyl, heterocycle, aryl, and heteroaryl; and a is a double bond either between Y—C or Z—C.

In a preferred embodiment of the compounds of formula I, $R^1$ is selected from the group consisting of
—H,
—$NR^4R^5$,
lower alkyl which optionally may be substituted by $R^{11}$, cyctoalkyl, heterocycle, aryl, and heteroaryl, and wherein the cycloalkyl and heterocycle optionally may be substituted by $R^{11}$ and the aryl and heteroaryl optionally may be substituted by $R^{12}$, cycloalkyl which optionally may be substituted by $R^{11}$, lower alkyl, heterocycle, aryl, and heteroaryl, and wherein the lower alkyl and heterocycle optionally may be substituted by $R^{11}$ and the aryl and heteroaryl optionally may be substituted by $R^{12}$, heterocycle which optionally may be substituted by $R^{11}$, lower alkyl, cycloalkyl, aryl, and heteroaryl, and wherein the lower alkyl and cycloalkyl optionally may be substituted by $R^{11}$ and the aryl and heteroaryl optionally may be substituted by $R^{12}$, aryl which optionally may be substituted by $R^{12}$, lower alkyl, cycloatkyt, heterocycle, aryl, and heteroaryl, and wherein the lower alkyl, heterocycle, and cycloalkyl optionally may substituted by $R^{11}$ and the aryl and heteroaryl optionally may be substituted by $R^{12}$, and heteroaryl which optionally may be substituted by $R^{12}$, lower alkyl, cycloatkyl, heterocycle, heteroaryl, and aryl, and wherein the lower alkyl, heterocycle, and cycloalkyl optionally may be substituted by $R^{11}$ and the heteroaryl and aryl optionally may be substituted by $R^{12}$.

In another preferred embodiment of the compounds of formula I, $R^2$ is selected from the group consisting of
—H,
—$OR^3$,
—$NR^4R^5$, and
lower alkyl which optionally may be substituted by the group consisting of —$OR^3$ and —$NR^4R^5$.

In a more preferred embodiment of the compounds of formula I, $R^1$ is selected from the group consisting of
—H,
—$NR^4R^5$,
lower alkyl which optionally may be substituted by $R^{11}$, heterocycle, aryl and heteroaryl, wherein the heterocycle may be optionally substituted by $R^{11}$, and the aryl and heteroaryl optionally may be substituted by $R^{12}$, aryl which optionally may be substituted by $R^{12}$ and lower alkyl wherein the lower alkyl optionally may be further substituted by $R^{11}$; and heteroaryl which optionally may be substituted by $R^{12}$ and lower alkyl wherein the lower alkyl optionally may be further substituted by $R^{11}$; and $R^2$ is selected from the group consisting of
—H,
—$OR^8$, and
lower alkyl which optionally may be substituted by the group consisting of —$OR^8$ and —$NR^8R^9$.

In another preferred embodiment of the compounds of formula I, both Y and Z are N.

The following are examples of preferred compounds of the invention:

2-Phenyl-6,8-dihydro-oxazolo[4,5-e]indol-7-one (A),
2-Phenyl-6,8-dihydro-thiazolo[4,5-e]indol-7-one (B),
2-Phenyl-6,8-dihydro-oxazolo[5,4-e]indol-7-one (C),
2-Phenyl-6,8-dihydro-thiazolo[5,4-e]indol-7-one (D),
(Z)-1,3-Dihydro-4-fluoro-5-nitro-3-[(1H-pyrrol-2-yl)methylene]-2H-indol-2-one (I),
(Z)-4-Azido-1,3-dihydro-5-nitro-3-[(1H-pyrrol-2-yl)methylene]-2H-indol-2-one (J),
(Z)-4,5-Diamino-1,3-dihydro-3-[(1H-pyrrol-2-yl)methylene]-2H-indol-2-one (K),
(Z)-1,3-Dihydro-4-fluoro-3-[(3-methoxy-1H-pyrrol-2-yl)methylene]-5-nitro-2H-indol-2-one (L),
(Z)-4-Azido-1,3-dihydro-3-[(3-methoxy-1H-pyrrol-2-yl)methylene]-5-nitro-2H-indol-2-one (M),
(Z)-4,5-Diamino-1,3-dihydro-3-[(3-methoxy-1H-pyrrol-2-yl)methylene]-2H-indol-2-one (N),
(Z)-1,3-Dihydro-4-fluoro-3-[(4-methyl-1H-imidazol-5-yl)methylene]-5-nitro-2H-indol-2-one (OO),
(Z)-4-Azido-1,3-dihydro-3-[(4-methyl-1H-imidazol-5-yl)methylene]-5-nitro-2H-indol-2-one (PP),
(Z)-4-Amino-1,3-dihydro-3-[(4-methyl-1H-imidazol-5-yl)methylene]-5-nitro-2H-indol-2-one (QQ),
(Z)-4,5-Diamino-1,3-dihydro-3-[(4-methyl-1H-imidazol-5-yl)methylene]-2H-indol-2-one (RR).

Additional preferred compounds include:

(Z)-6,8-dihydro-8-[(3-methoxy-1H-pyrrol-2-yl)methylene]-2-phenyl-7H-pyrrolo[3,2-e]benzoxazol-7-one (E),
(Z)-6,8-dihydro-8-[(3-methoxy-1H-pyrrol-2-yl)methylene]-2-phenyl-7H-pyrrolo[3,2-e]benzothiazol-7-one (F),
(Z)-6,8-dihydro-8-[(3-methoxy-1H-pyrrol-2-yl)methylene]-2-phenyl-7H-pyrrolo[2,3-g]benzoxazol-7-one (G),
(Z)-6,8-dihydro-8-[(3-methoxy-1H-pyrrol-2-yl)methylene]-2-phenyl-7H-pyrrolo[2,3-g]benzothiazol-7-one (H),
(Z)-8-[(3-Methoxy-1H-pyrrol-2-yl)methylene]-2-methyl-3,6,7,8-tetrahydro-pyrrolo-[3,2-e]benzimidazol-7-one (P),
(Z)-2-[(4-Methoxyphenyl)methyl]-8-[(3-methoxy-1H-pyrrol-2-yl)methylene]-3,6,7,8-tetrahydro-pyrrolo[3,2-e]benzimidazol-7-one (T),
rac-(Z)-2-(1-Hydroxy-1-phenyl-methyl)-8-[(3-methoxy-1H-pyrrol-2-yl)methylene]-3,6,7,8-tetrahydro-pyrrolo[3,2-e]benzimidazol-7-one (U),
(Z)-2-[2-(4-hydroxyphenyl)ethyl]-8-[(3-methoxy-1H-pyrrol-2-yl)methylene]-3,6,7,8-tetrahydro-pyrrolo[3,2-e]benzimidazol-7-one (V),
(Z)-2-[3-(phenyl)propyl]-8-[(3-methoxy-1H-pyrrol-2-yl)methylene]-3,6,7,8-tetrahydro-pyrrolo[3,2-e]benzimidazol-7-one (W),
(Z)-8-[(4-Methyl-1H-imidazol-5-yl)methylene]-3,6,7,8-tetrahydro-pyrrolo[3,2-e]benzimidazol-7-one (SS),
(Z)-8-[(3-Methoxy-1H-pyrrol-2-yl)methylene]-3,6,7,8-tetrahydro-pyrrolo-[3,2-e]benzimidazol-7-one (TT),
(Z)-2-Phenyl-8-[(1H-pyrrol-2-yl)methylene]-3,6,7,8-tetrahydro-pyrrolo[3,2-e]benz-imidazol-7-one (O),
(Z)-8-[(3-Methoxy-1H-pyrrol-2-yl)methylene]-2-phenyl-3,6,7,8-tetrahydro-pyrrolo[3,2-e]benzimidazol-7-one (Q),
(Z)-4-[8-[(3-Methoxy-1H-pyrrol-2-yl)methylene]-3,6,7,8-tetrahydro-pyrrolo[3,2-e]-benzimidazol-2-yl]benzoic acid (R),
(Z)-2-(2-Hydroxyphenyl)-8-[(3-methoxy-1H-pyrrol-2-yl)methylene]-3,6,7,8-tetrahydro-pyrrolo[3,2-e]benzimidazol-7-one (S),
(Z)-2-[N-(3-Methoxypropyl)amino]-8-[(3-methoxy-1H-pyrrol-2-yl)methylene]-3,6,7,8-tetrahydro-pyrrolo[3,2-e]benzimidazol-7-one (X),
(Z)-2-[N-[(4-Methoxyphenyl)methyl]amino]-8-[(3-methoxy-1H-pyrrol-2-yl)methylene]-3,6,7,8-tetrahydro-pyrrolo[3,2-e]benzimidazot-7-one (AA),
(Z)-2-[N-[(4-Fluorophenyl)methyl]amino]-8-[(3-methoxy-1H-pyrrol-2-yl)methylene]-3,6,7,8-tetrahydro-pyrrolo[3,2-e]benzimidazol-7-one (FF),
(Z)-2-[N-[2-(3,4-Dimethoxyphenyl)ethyl]amino]-8-[(3-methoxy-1H-pyrrol-2-yl)methylene]-3,6,7,8-tetrahydro-pyrrolo[3,2-e]benzimidazol-7-one (GG),
rac-(Z)-8-[(3-Methoxy-1H-pyrrol-2-yl)methylene]-2-[N-(1-phenylethyl)amino]-3,6,7,8-tetrahydro-pyrrolo[3,2-e]benzimidazol-7-one (HH),
(Z)-8-[(3-Methoxy-1H-pyrrol-2-yl)methylene]-2-[N-(4-phenylbutyl)amino]-3,6,7,8-tetrahydro-pyrrolo[3,2-e]benzimidazol-7-one (JJ),
(Z)-8-[(3-Methoxy-1H-pyrrol-2-yl)methyLene]-2-[N-[(2-tetrahydrofuranyl)methyl]-amino]-3,6,7,8-tetrahydro-pyrrolo[3,2-e]benzimidazol-7-one (KK),
(Z)-4-[[8-[(3-Methoxy-1H-pyrrol-2-yl)methylene]-7-oxo-3,6,7,8-tetrahydro-imidazo[4,5-e]indol-2-yl]amino]-butanoic acid ethyl ester (LL),
(Z)-8-[(3-Methoxy-1H-pyrrol-2-yl)methylene]-2-[N-[2-(N-piperidinyl)ethyl]-amino]-3,6,7,8-tetrahydro-pyrrolo[3,2-e]benzimidazol-7-one (NN),
(Z)-2-[N-(1,3-Benzodioxol-5-yl)methylamino]-8-[(3-methoxy-1H-pyrrol-2-yl)methylene]-3,6,7,8-tetrahydro-pyrrolo[3,2-e]benzimidazol-7-one (VV),
(Z)-8-[(3-Methoxy-1H-pyrrol-2-yl)methylene]-2-[N-(1-naphthalenyl)methylamino]-3,6,7,8-tetrahydro-pyrrolo[3,2-e]benzimidazol-7-one (WW),
(Z)-8-[(3-Methoxy-1H-pyrrol-2-yl)methylene]-2-[N-(3-phenylpropyl)amino]-3,6,7,8-tetrahydro-pyrrolo[3,2-e]benzimidazol-7-one (XX),
(Z)-2-[N-(3,4-Dimethoxyphenyl)amino]-8-[(3-methoxy-1H-pyrrol-2-yl)methylene]-3,6,7,8-tetrahydro-pyrrolo[3,2-e]benzimidazol-7-one (Y),
(Z)-2-[N-(4-Methoxyphenyl)amino]-8-[(3-methoxy-1H-pyrrol-2-yl)methylene]-3,6,7,8-tetrahydro-pyrrolo[3,2-e]benzimidazol-7-one (Z),
(Z)-2-[N-(3-Acetylphenyl)amino]-8-[(3-methoxy-1H-pyrrol-2-yl)methylene]-3,6,7,8-tetrahydro-pyrrolo[3,2-e]benzimidazol-7-one (BB),
(Z)-4-[[8-[(3-Methoxy-1H-pyrrol-2-yl)methylene]-7-oxo-3,6,7,8-tetrahydro-imidazo[4,5-e]indol-2-yl]amino]-benzoic acid ethyl ester (CC),
(Z)-2-[N-(4-Dimethylaminophenyl)amino]-8-[(3-methoxy-1H-pyrrol-2-yl)methylene]-3,6,7,8-tetrahydro-pyrrolo[3,2-e]benzimidazol-7-one (DD), (Z)-4-[[8-[(3-Methoxy-1H-pyrrol-2-yl)methylene]-7-oxo-3,6,7,8-tetrahydro-imidazo[4,5-e]indol-2-yl]amino]-benzoic acid methyl ester (EE), (Z)-2-[N-(2-Methoxyphenyl)amino]-8-[(3-methoxy-1H-pyrrol-2-yl)methylene]-3,6,7,8-tetrahydro-pyrrolo[3,2-e]benzimidazol-7-one (II), (Z)-8-[(3-Methoxy-1H-pyrrol-2-yl)methylene]-2-[N-(1-naphthyl)amino]-3,6,7,8-tetrahydro-pyrrolo[3,2-e]benzimidazol-7-one (MM), (Z)-8-[(3-Methoxy-1H-pyrrol-2-yl)methylene]-2-[N-[4-phenyl-(2-methoxyphenyl)]amino]-3,6,7,8-tetrahydro-pyrrolo[3,2-e]benzimidazol-7-one (UU), (Z)-2-[N-(2,3-Dihydro-1H-inden-5-yl)amino]-8-[(3-methoxy-1H-pyrrol-2-yl)methylene]-3,6,7,8-tetrahydro-pyrrolo[3,2-e]benzimidazol-7-one (YY).

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds of Formula I

The compounds of formula I may be prepared by processes known in the art. Suitable processes for synthesizing these compounds are provided in the examples below. Generally, these compounds may be prepared according to the following synthesis schemes.

Method 1

Step A:

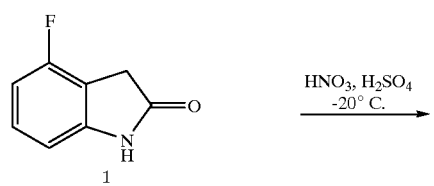

Step B:

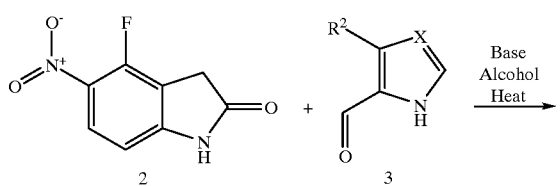

Step C:

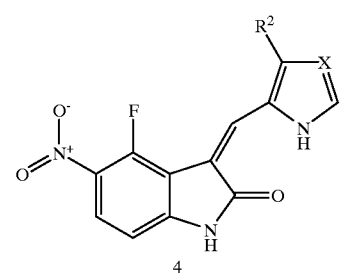

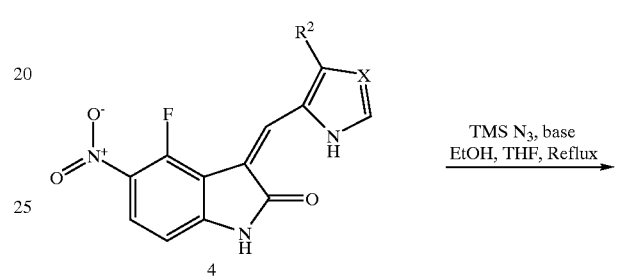

Step D:

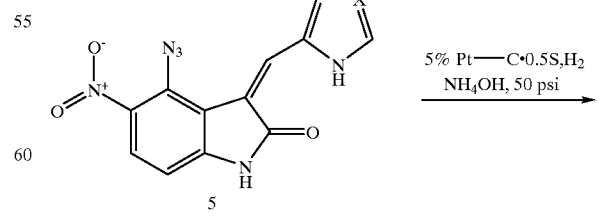

Method 3:
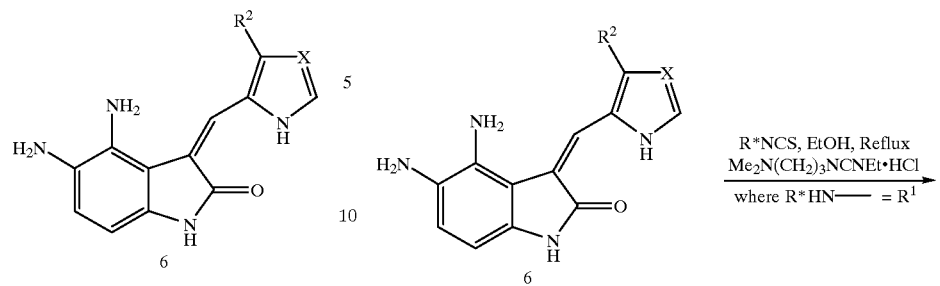
Step E:
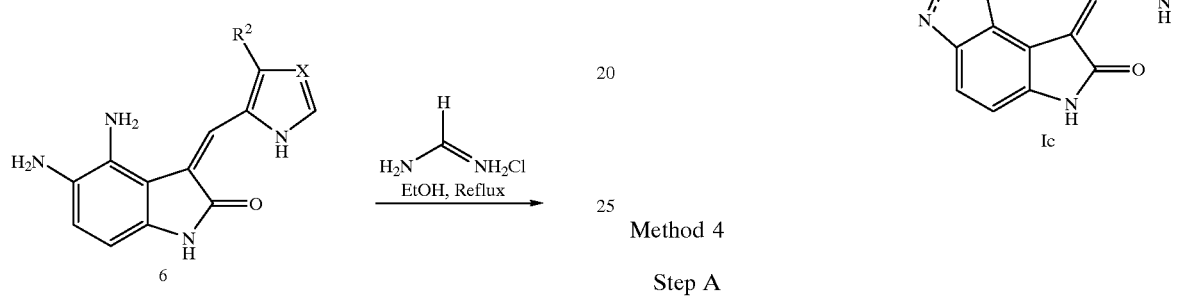
Method 2:
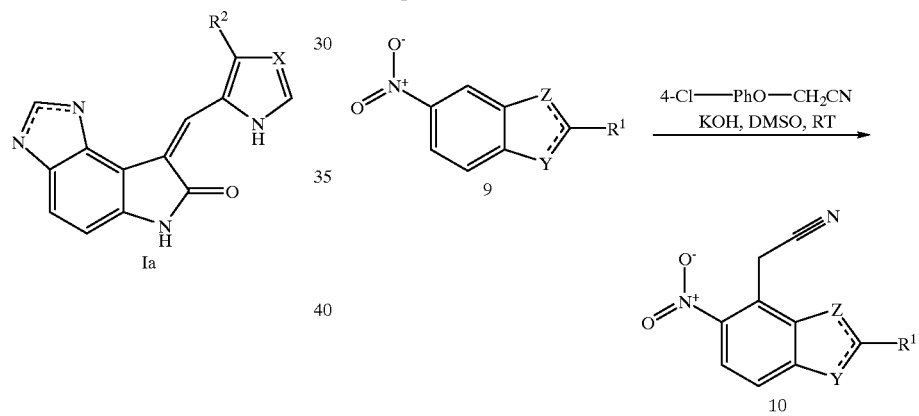
Method 4
Step A
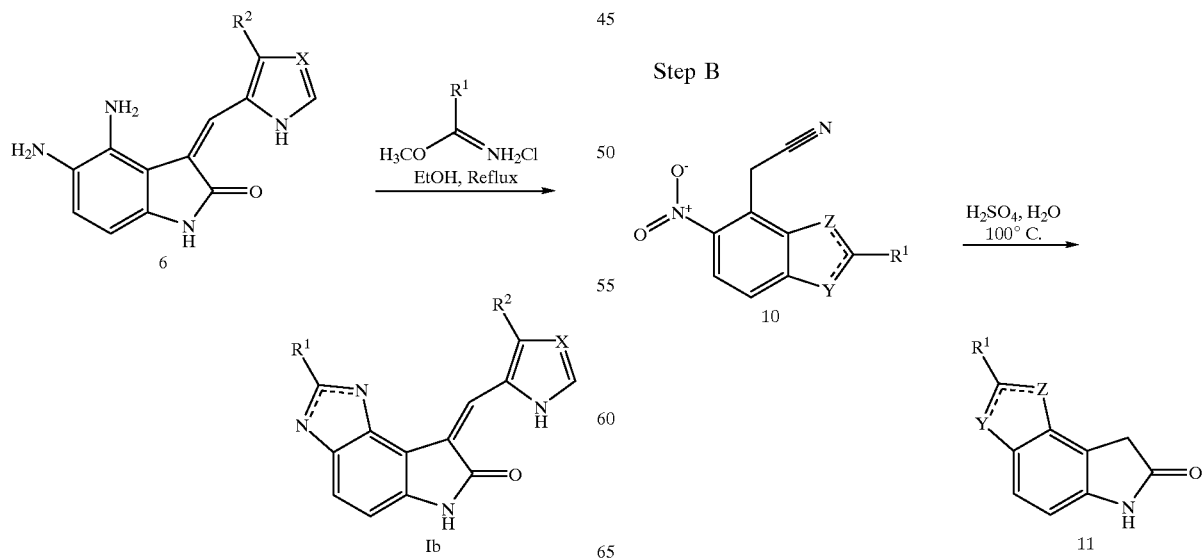
Step B Step C

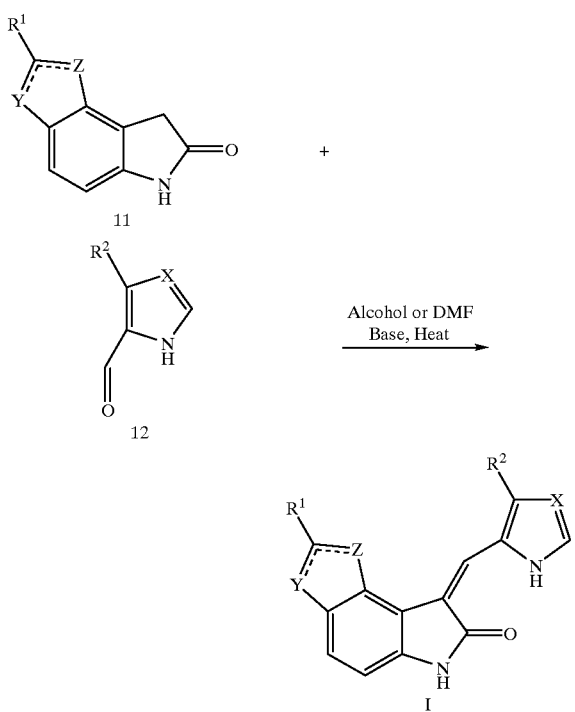

In Methods 1–3 above, Y and Z are both N. In Method 4, one of Y and Z is N and the other is O or S.

Compositions/Formulations

In an alternative embodiment, the present invention is directed to pharmaceutical compositions comprising at least one compound of formula I or a prodrug thereof, or a pharmaceutically acceptable salt of a compound of formula I or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid poll. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerin, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of formula I, prodrugs thereof, and their salts, and compositions containing these compounds are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound of formula I can vary within wide limits and will be adjusted to the individual requirements in each particular case. In general, in the case of oral or parenteral administration to adult humans weighing approximately 70 Kg, a daily dosage of about 10 mg to about 10,000 mg. preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as for example the general schemes provided above. The following examples illustrate preferred methods for synthesizing the compounds and formulations of the present invention.

Example 1

General Synthesis Steps and Starting Materials

General Method A: Preparation of substituted tricyclic benzimidazoles:

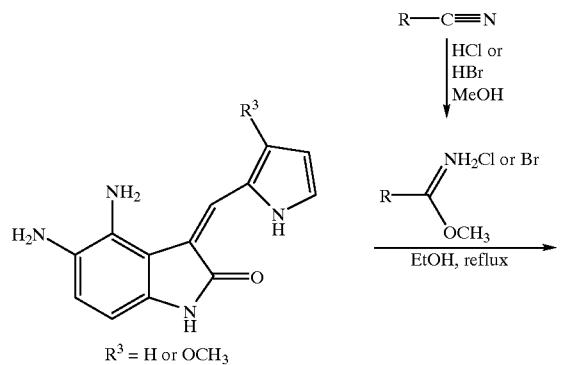

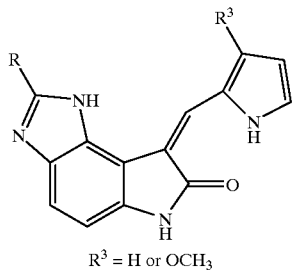

R³ = H or OCH₃

Step 1:

A solution of the nitrite (RCN, 2 g) in MeOH (20 mL) (all nitrites used in these examples were obtained from commercial sources) was cooled to 0° C. (ice water bath) and HCl or HBr gas was bubbled into the solution mixture. The disappearance of the starting nitrite was monitored by TLC. After total conversion, the mixture was concentrated under reduced pressure to afford the imidate as crude material which was used in the next step without further purification.

Step 2:

A mixture of diamino oxindoLe (0.22 mmol, 60 mg) and crude imidate (4 eq, 0.88 mmol) in ethanol (3 mL) was heated at reflux. The reaction was monitored by TLC. Complete conversion was usually achieved after 0.5 to 4 h. The reaction mixture was cooled to room temperature (r.t.), then quenched with 1N HCl. The resulting precipitate was collected by suction filtration, washed with water and dried in a vacuum oven. If necessary, the product was purified by reverse phase chromatography.

General Method B: Preparation of Substituted aminobenzymidazoles

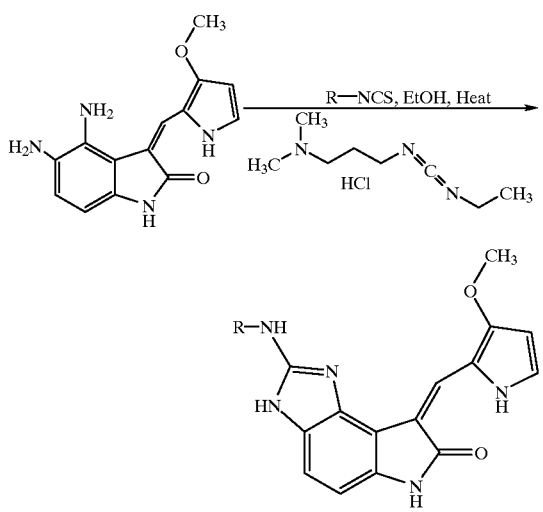

A heterogeneous mixture of a diamino oxindole (60 mg, 0.22 mmol) and an isothiocyanate (5 eq, 1.1 mmol) in ethanol (2 mL) was placed in a heavy walled glass tube. The coupling reagent N-(3-dimethylaminopropyl)-N'-ethylcarbodiimide hydrochloride (Fluka) was then added at r.t. (65 mg, 0.33 mmol). The tube was sealed with a teflon screw cap and placed in a heated oil bath at 94–98° C. The reaction was monitored by TLC. Reaction times ranged from 45 min to 12 hours. After completion of the reaction, the mixture was cooled to r.t. and quenched with water. If a precipitate was formed, Step 1 below was followed. Otherwise, Step 2 below was followed.

Step 1: The precipitate was collected by suction filtration, washed with water and dried in a vacuum oven. If necessary, purification was performed using reverse phase HPLC.

Step 2: The mixture was extracted with ethyl acetate. The phases were separated. The organic layer was washed with brine, dried over anhydrous sodium sulfate and concentrated under reduced pressure. The residue was triturated with ether, and the resulting solid was collected by suction filtration. If necessary, the product was purified by reverse phase HPLC.

Starting Material 1: 5-Nitro-2-phenyl-benzothiazole

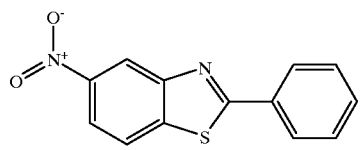

2-Chloro-5-nitroaniline (2.00 g, 11.8 mmol) (Aldrich), benzoyl chloride (1.98 g, 14.2 mmol)(J. T. Baker), triethylamine ("TEA", 1.79 g, 17.7 mmol)(Aldrich), and a few crystals of 4-dimethylaminopyridine ("DMAP", Aldrich) were combined in 100 mL of dichloromethane at 0° C. The mixture was allowed to warm to room temperature and was stirred at room temperature for 16 hours. The mixture was washed with dilute hydrochloric acid solution, water, saturated sodium bicarbonate solution, brine and dried over anhydrous sodium sulfate. The solvent was concentrated to give 2.57 g of a solid which was combined with absolute ethanol and heated at reflux. Subsequently, a mixture of sulfur (310 mg) and sodium sulfide (2.23 g) was heated (heatgun) to form a granular solid. This solid mixture was added to the refluxing ethanolic mixture and refluxing was continued for 6 hours. The mixture was cooled, acidified with concentrated hydrochloric acid, and poured into water. The aqueous mixture was extracted three times with ethyl acetate. The combined organic extracts were washed with water, brine and dried over anhydrous magnesium sulfate. Concentration of the solution gave 1.52 grams of a yellow solid that was used without further purification.

Starting Material 2: 5-Nitro-2-phenyl-benzoxazole

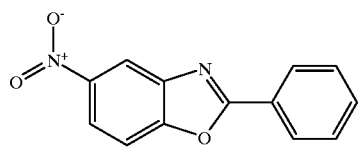

2-Amino-4-nitrophenol (1.00 g, 6.49 mmol)(Aldrich), trimethylorthobenzoate (1.42 g, 7.79 mmol)(Aldrich), and 50 mg p-toluene sulfonic acid monohydrate (Aldrich) were mixed in 30 mL of benzene. The mixture was heated at reflux for 3 hours, cooled, diluted with 30 mL hexanes, and filtered. The solid residue was crystallized from EtOAc/Hexanes to give 1.30 g (5.42 mmol, 83%) of a greenish yellow solid that was used without further purification.

Starting Material 3: 6-Nitro-2-phenyl-benzoxazole

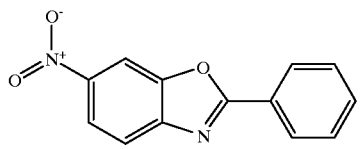

2-Amino-5-nitrophenol (1.00 g, 6.49 mmol)(Aldrich), trimethylorthobenzoate (1.42 g, 7.79 mmol)(Aldrich), and 50 mg p-toluene sulfonic acid monohydrate (Aldrich) were mixed in 30 mL of benzene. The mixture was refluxed for 3 hours, cooled, diluted with 30 mL hexane, and filtered. The solid residue was crystallized from EtOAc/Hexanes to give 1.32 g (5.52 mmol, 85%) of a green solid.

Starting Material 4: 6-Nitro-2-phenyl-benzothiazole

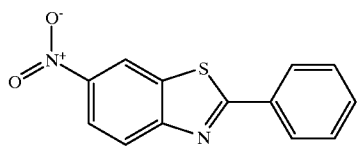

To a stirred mixture of 2-phenyl-benzothiazole (1.05 g, 4.97 mmol)(Lancaster) in concentrated $H_2SO_4$ (10 mL) was added a solution of $HNO_3$ (0.35 mL) and $H_2SO_4$ (1.8 mL) at −5° C. The reaction mixture was stirred at −5° C. for 2 h, poured into ice and extracted with EtOAc (3×50 mL). The combined extracts were washed with brine, dried over anhydrous $MgSO_4$ and concentrated in vacuo. The residue was purified on a silica gel column eluting with Hex/EtOAc=5/1 to give 0.802 g (3.13 mmol, 63%) of a white solid.

Starting Material 5: (5-Nitro-2-phenyl-benzoxazole-4-yl)-acetonitrile

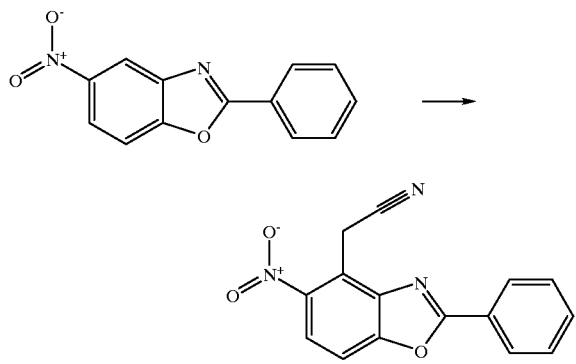

5-Nitro-2-phenyl-benzoxazole (300 mg, 1.25 mmol) (Starting Material 2) and 4-chlorophenoxyacetonitrile (219 mg, 1.3 mmol) (Aldrich) were mixed in dimethylsulfoxide (3.5 mL). Powdered potassium hydroxide (276 mg, 5 mmol) was added and the mixture was stirred at room temperature for 2.25 hours. The mixture was poured into ice water and acidified with concentrated hydrochloric acid. The mixture was extracted with ethyl acetate (3×). The combined organic layers were washed with water (2×), brine and dried over anhydrous magnesium sulfate. The solvent was concentrated in vacuo and the residue was crystallized from ethyl acetate/hexanes to give the product. (Yield 114 mg, 33%).

Starting Material 6: (5-Nitro-2-phenyl-benzothiazole-4-yl)-acetonitrile

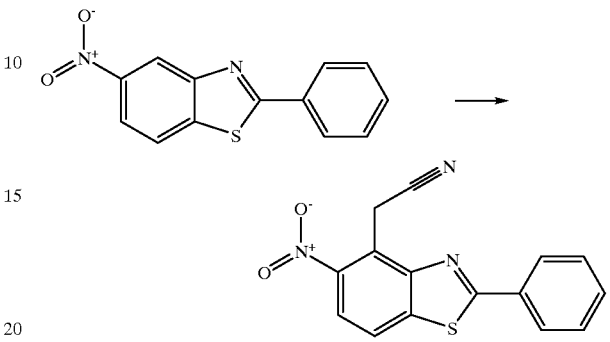

5-Nitro-2-phenyl-benzothiazole (1.52 g, 5.94 mmol) (Starting Material 1) and 4-chlorophenoxyacetonitrile (1.05 g, 6.26 mmol) (Aldrich) were mixed in dimethylsulfoxide (20 mL). Powdered potassium hydroxide (1.40 g, 25 mmol) was added, and the mixture was stirred at room temperature for 8 hours. The mixture was poured into ice water and acidified with concentrated hydrochloric acid. The mixture was extracted with ethyl acetate (3×). The combined organic layers were washed with water (2×), brine and dried over anhydrous magnesium sulfate. The solvent was concentrated in vacuo and the residue was crystallized from ethyl acetate/hexanes to give the product. (Yield 0.64 g, 37%).

Starting Material 7: (6-Nitro-2-phenyl-benzoxazole-7-yl)-acetonitrile

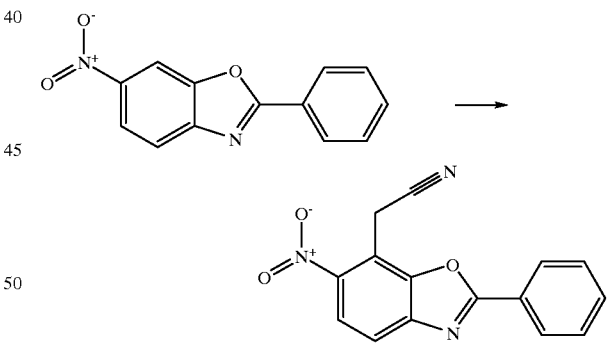

To a stirred suspension of potassium tert-butoxide (701 mg, 6.25 mmol) in DMF (6 mL) was added a solution of 6-nitro-2-phenyl-benzoxazole (500 mg, 2.08 mmol) (Starting Material 3) and 4-chlorophenoxyacetonitrile (366 mg, 2.19 mmol) (Aldrich) in DMF (20 mL) at −30° C. The mixture was then stirred at this temperature for 3 h and neutralized with aqueous 1N hydrochloric acid solution at 0° C. The aqueous layer was extracted with ethyl acetate. The combined extracts were dried over anhydrous magnesium sulfate and concentrated in vacuo to give a yellow solid. The crude product was purified by silica gel chromatography. (Yield 520 mg, 90%).

Starting Material 8: (6-Nitro-2-phenyl-benzothiazole-7-yl)-acetonitrile

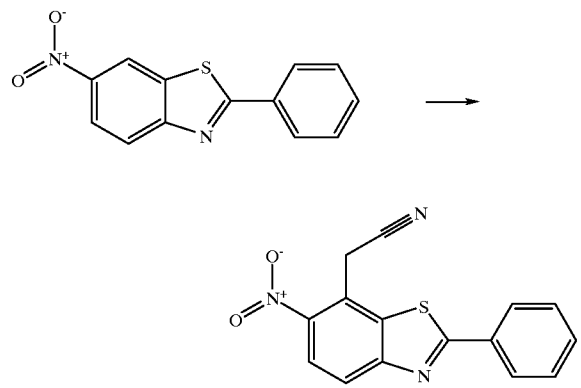

To a stirred suspension of potassium tert-butoxide (171 mg, 1.53 mmol) (Aldrich) in DMF (2 mL) was added a solution of 6-nitro-2-phenyl-benzothiazole (130 mg, 0.51 mmol) (Starting Material 4) and 4-chlorophenoxyacetonitrile (89.4 mg, 0.53 mmol)(Aldrich) in DMF (7 mL) at −30° C. The mixture was then stirred at this temperature for 3 h and neutralized with aqueous 1N hydrochloric acid solution at 0° C. The aqueous layer was extracted with ethyl acetate. The combined extracts were dried over anhydrous magnesium sulfate and concentrated in vacuo to give a yellow solid. The crude product was purified by silica get chromatography. (Yield 42 mg, 28%).

Starting Material 9: 1,3-Dihydro-4-fluoro-2H-indol-2-one

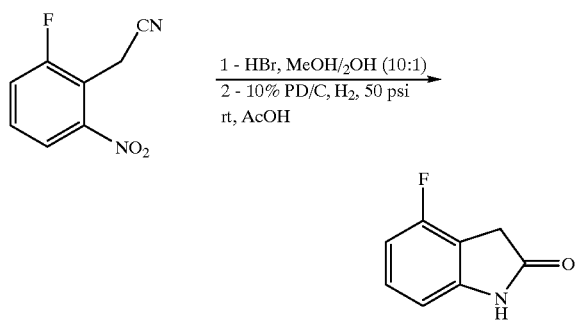

6-Fluoro-2-nitrobenzyl cyanide (23.10 g, 0.12 mole) (prepared according to A. Kalir, *Synthesis* (1987) 514–515) was dissolved in 10:1 MeOH/H$_2$O (250 mL) and the solution was chilled in an ice water bath. HBr gas was bubbled into the cold mixture for 75 min. The solution was allowed to warm up to r.t. and then concentrated to half its volume under reduced pressure. THF (100 mL), water (100 mL) and conc. HCl (6 mL) were successively added at r.t. and stirring was maintained for 75 min. The mixture was poured into water and extracted with ethyl acetate. The combined organic layers were washed with water, sat. aq. NaHCO$_3$ and brine, then dried over sodium sulfate and concentrated under educed pressure. This material (20.9 g) was dissolved in acetic acid (200 mL) and hydrogenated for 2 h in a Parr apparatus at 50 Psi, in the presence of 10% Pd/C (4.33 g). The reaction mixture was filtered through a cake of Celite®, and the cake was washed with acetic acid. The solution was concentrated under reduced pressure and dissolved in MeOH (300 mL) containing 1N NaOH (15 mL). This mixture was poured into 2:1 sat aq. NaCl/H$_2$O (600 mL) and extracted with ethyl acetate. The combined organic layers were washed with brine, dried over sodium sulfate and concentrated. The crude residue was triturated with ether to afford 5.8 g (first crop) of pure 1,3-dihydro-4-fluoro-2H-indol-2-one. The mother liquor was chromatographed on Silica Gel (230–400 mesh, eluted with 40% ethyl acetate in hexanes) to yield 16 g of product (overall yield from cyanide: 41%).

Starting Material 10: 1,3-Dihydro-4-fluoro-5-nitro-2H-indol-2-one

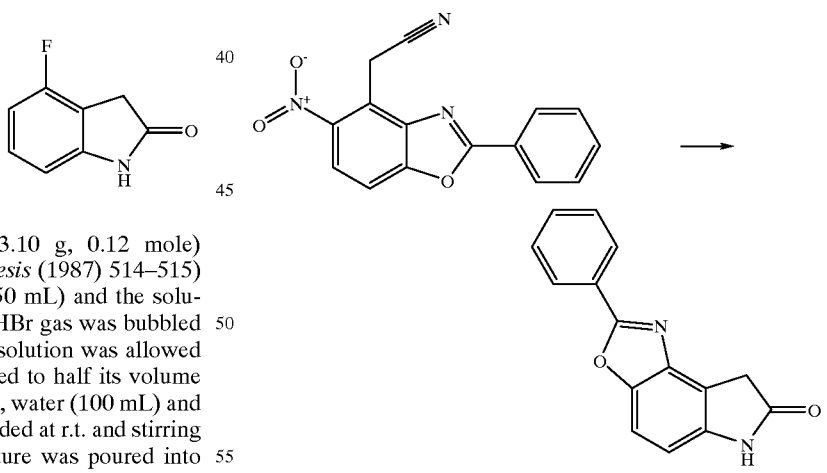

1,3-Dihydro-4-fluoro-2H-indol-2-one (6.29g, 41.6 mmol) (Starting Material 9) was dissolved in 100 mL conc. H$_2$SO$_4$ with stirring. This mixture was cooled in a dry ice-acetone bath to −20° C. to which was added slowly over 30 min. a solution of 2.6 mL (41.6 mmol) HNO$_3$ in 10 mL H$_2$SO$_4$. The reaction mixture was stirred at −20° C. for 45 min. after addition (TLC: 50% ethyl acetate in hexanes showed complete reaction after 30 min.), then poured into 1 L ice and water, extracted with 2×200 mL ethyl acetate, washed with 2×200 mL sat. NaCl solution, dried over Na$_2$SO$_4$, filtered and concentrated at 45° C. under high vacuum to give a brown solid (7.87 g). Crystallization from ethyl acetate gave a brown solid (3.94 g). The mother liquor was chromatographed on Silica Gel (230–400 mesh, eluted with 50% ethyl acetate in hexanes) to give 1.91 g of additional product. (Total yield 5.85 g, 71.7%).

Example 2

2-Phenyl-6,8-dihydro-oxazolo[4,5-e]indol-7-one (A)

A solution of (5-nitro-2-phenyl-benzoxazole-4-yl)-acetonitrile (1.10 g, 3.98 mmol) (Starting Material 5) was suspended in concentrated H$_2$SO$_4$/H$_2$O (1/1, 25 mL) and stirred at 100° C. for 30 min. The resulting solution was diluted with water and extracted with ethyl acetate, and the combined organic extracts were dried over anhydrous magnesium sulfate and concentrated in vacuo to give the crude acid.

To a solution of the crude acid in acetic acid (10 mL) heated at reflux was added excess zinc dust (1.57 g, 24.2 mmol) portionwise during thirty minutes or until the reaction solution clarified. The mixture was filtered through a Celite® (Fisher Scientific) pad and washed with hot DMF. The solvent was removed in vacuo and residue was suspended and stirred for 30 minutes in 3M hydrochloric acid. The insoluble solid material was collected, washed with water, and air dried to give 2-phenyl-6,8-dihydro-oxazolo[4,5-e]indol-7-one. (Yield 180 mg, 18%)

Example 3

2-Phenyl-6,8-dihydro-thiazolo[4,5-e]indol-7-one (B)

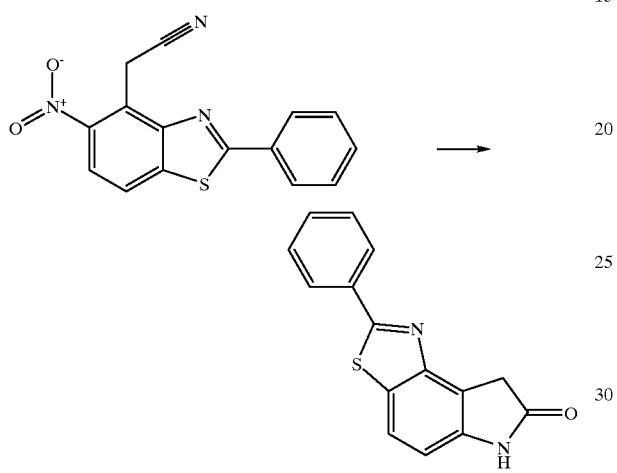

A solution of (5-nitro-2-phenyl-benzothiazole-4-yl)-acetonitrile (204.2 mg 0.692 mmol) (Starting Material 6) was suspended in concentrated $H_2SO_4/H_2O$ (1/1, 3 mL)) and stirred at 100° C. for 30 min. The resulting solution was diluted with water and extracted with ethyl acetate, and the combined organic extracts were dried over anhydrous magnesium sulfate and concentrated in vacuo to give the crude acid. To a solution of the crude acid in acetic acid (5 mL) heated at reflux was added excess zinc dust (0.45 g, 6.92 mmol) portionwise during thirty minutes. The mixture was filtered through a Celite® pad and washed with hot DMF. The solvent was removed in vacuo and residue was suspended and stirred for 30 minutes in 3M hydrochloric acid. The insoluble solid material was collected, washed with water, and air dried to give 2-phenyl-6,8-dihydro-thiazolo[4,5-e]indol-7-one. (Yield 20 mg, 11%)

Example 4

2-Phenyl-6,8-dihydro-oxazolo[5,4-e]indol-7-one (C)

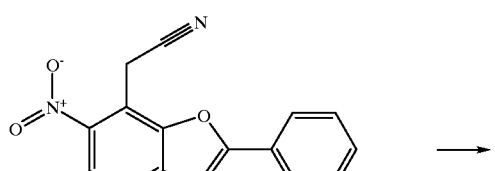

-continued

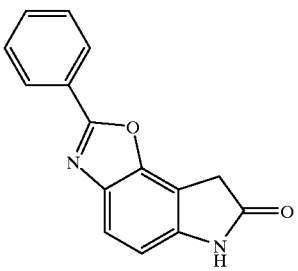

A solution of (6-nitro-2-phenyl-benzoxazole-7-yl)-acetonitrile (66 mg 0.23 mmol) (Starting Material 7) was suspended in concentrated $H_2SO_4/H_2O$ (1/1, 2 mL)) and stirred at 100° C. for 30 min. The resulting solution was diluted with water and extracted with ethyl acetate, and the combined organic extracts were dried over anhydrous magnesium sulfate and concentrated in vacuo to give the crude acid. To a solution of the crude acid in acetic acid (3 mL) heated at reflux was added excess zinc dust (120 mg, 1.85 mmol) portionwise during thirty minutes. The mixture was filtered through a Celite® pad and washed with hot DMF. The solvent was removed in vacuo and residue was suspended and stirred for 30 minutes in 3M hydrochloric acid. The insoluble solid material was collected, washed with water, and air dried to give 2-phenyl-6,8-dihydro-oxazolo[5,4-e]indol-7-one. (Yield 17 mg, 30%)

Example 5

2-Phenyl-6,8-dihydro-thiazolo[5,4-e]indol-7-one (D)

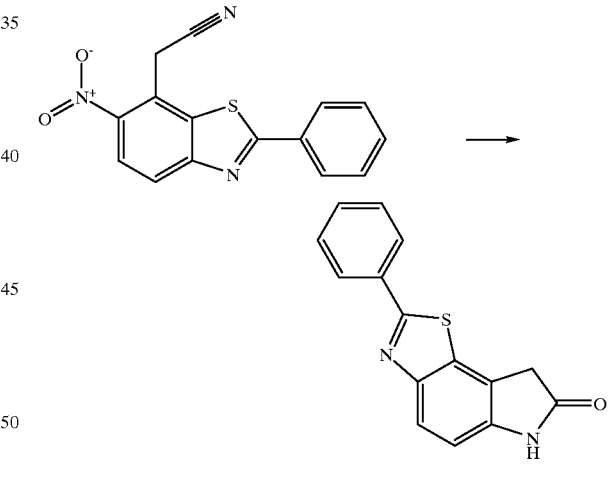

A solution of (6-nitro-2-phenyl-benzothiazole-7-yl)-acetonitrile (40 mg 0.23 mmol) (Starting Material 8) was suspended in concentrated $H_2SO_4/H_2O$ (1/1, 2 mL) and stirred at 100° C. for 30 min. The resulting solution was diluted with water and extracted with ethyl acetate, and the combined organic extracts were dried over anhydrous magnesium sulfate and concentrated in vacuo to give the crude acid. Subsequently, to a solution of the crude acid in acetic acid (3 mL) heated at reflux was added excess zinc dust (88.4 mg, 1.36 mmol) portionwise during thirty minutes. The mixture was filtered through a Celite® pad and washed with hot DMF. The solvent was removed in vacuo and residue was suspended and stirred for 30 minutes in 3M hydrochloric acid. The insoluble solid material was collected, washed with water, and air dried to give 2-phenyl-6,8-dihydro-thiazolo[5,4-e]indol-7-one. (Yield 12 mg, 33%)

Example 6

(Z)-6,8-dihydro-8-[(3-methoxy-1H-pyrrol-2-yl)methylene]-2-phenyl-7H-pyrrolo[3,2-e]benzoxazol-7-one (E)

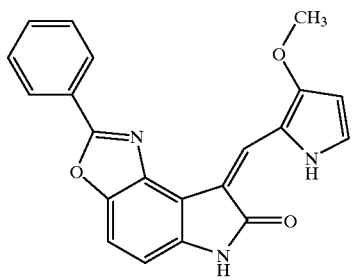

3-Methoxypyrrole-2-carboxaldehyde (15 mg, 0.12 mmol) (prepared according to F. Bellamy et. al., *J. Chem. Research* (S) (1979), 18–19; *J. Chem Research* (M) (1979) 0101–0116), piperidine (3 drops)(Aldrich), and 2-phenyl-6,8-dihydro-oxazolo[4,5-e]indol-7-one (25 mg, 0.10 mmol) (from Example 2) were dissolved in DMF (1 mL). The mixture was heated to 90° C. and stirred at that temperature for 1 h. The mixture was cooled, poured into water, and acidified with concentrated hydrochloric acid. The mixture was extracted with ethyl acetate, and the combined organic extracts were washed with water, brine, and dried over anhydrous magnesium sulfate. The solvent was concentrated under reduced pressure, and the crude product was purified by reverse phase HPLC with acetonitrile—water mixture as solvent. (Yield 3.6 mg, 8.4%)

Example 7

(Z)-6,8-dihydro-8-[(3-methoxy-1H-pyrrol-2-yl)methylene]-2-phenyl-7H-pyrrolo[3,2-e]benzothiazol-7-one (F)

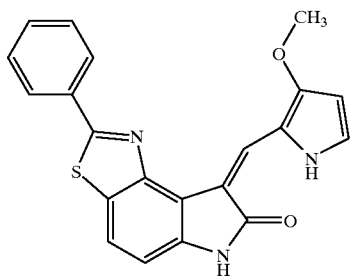

3-Methoxypyrrole-2-carboxaldehyde (11 mg, 0.088 mmol)(Bellamy, supra), piperidine (3 drops)(Aldrich), and 2-phenyl-6,8-dihydro-thiazolo[4,5-e]indol-7-one (21.4 mg, 0.08 mmol) (Example 3) were dissolved in DMF (3 mL). The mixture was heated to 90° C. and stirred at that temperature for 1 h. The mixture was cooled, poured into water, and acidified with concentrated hydrochloric acid. The mixture was extracted with ethyl acetate, and the combined organic extracts were washed with water, brine, and dried over anhydrous magnesium sulfate. The solvent was concentrated under reduced pressure, and the crude product was purified by reverse phase HPLC using acetonitrile—water as solvent, then crystallization from ethanol. (Yield 4.5 mg, 15%)

Example 8

(Z)-6,8-dihydro-8-[(3-methoxy-1H-pyrrol-2-yl)methylene]-2-phenyl-7H-pyrrolo[2,3-g]benzoxazol-7-one (G)

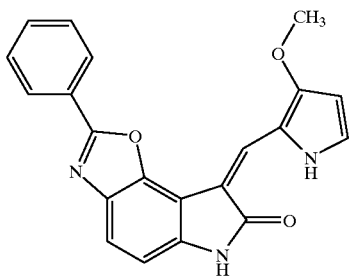

3-Methoxypyrrole-2-carboxaldehyde (13 mg, 0.105 mmol)(Bellamy, supra) and 2-phenyl-6,8-dihydro-oxazolo[5,4-e]-indol-7-one (17 mg, 0.068 mmol)(Starting Material 4) were suspended in a solution of 10% piperidine (Aldrich) in 2-propanol (1 mL). The mixture was heated at reflux for 2 h. The mixture was cooled, poured into water, and the aqueous mixture was made acidic with concentrated hydrochloric acid. The aqueous layer was extracted with ethyl acetate, and the combined organic extracts were washed with water, brine, and dried over anhydrous magnesium sulfate. The solvent was removed in vacuo and the crude product was purified by reverse phase HPLC using acetonitrile—water as solvent. (Yield 10 mg, 41%).

Example 9

(Z)-6,8-dihydro-8-[(3-methoxy-1H-pyrrol-2-yl)methylene]-2-phenyl-7H-pyrrolo[2,3-g]benzothiazol-7-one (H)

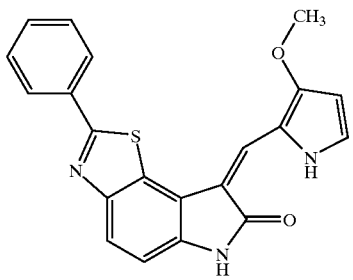

3-Methoxypyrrole-2-carboxaldehyde (13mg, 0.105 mmol) (Bellamy, supra) and 2-phenyl-6,8-dihydro-thiazolo[5,4-e]indol-7-one (20 mg, 0.075 mmol) (from Example 5) were suspended in a solution of 10% piperidine in 2-propanol (1 mL). The mixture was heated at reflux for 3 h. The mixture was cooled, poured into water, and the aqueous mixture was made acidic with concentrated hydrochloric acid. The aqueous layer was extracted with ethyl acetate, and the combined organic extracts were washed with water, brine, and dried over anhydrous magnesium sulfate. The solvent was removed in vacuo, and the crude product was purified by reverse phase HPLC using acetonitrile—water as solvent. (Yield 10 mg, 36%).

Example 10

(Z)-1,3-Dihydro-4-fluoro-5-nitro-3-[(1H-pyrrol-2-yl)methylene]-2H-indol-2-one (I)

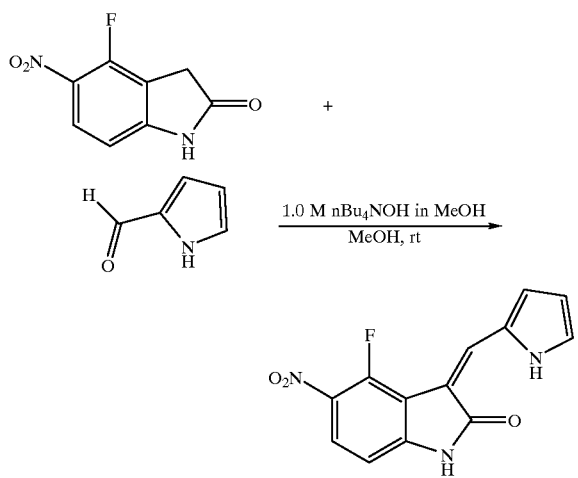

To a solution of 1,3-dihydro-4-fluoro-5-nitro-2H-indol-2-one (400 mg, 2.04 mmol) (Starting Material 10) in MeOH (4 mL), was successively added at room temperature pyrrole-2-carboxaldehyde (220 mg, 2.25 mmol) (Aldrich) and tetrabutyl ammonium hydroxide (4.5 mL, 1.0 M solution in MeOH)(Aldrich). The mixture was stirred at r.t. for 12 h, then quenched with 1N HCl. The yellow precipitate was collected by suction filtration, washed with water and dried in a vacuum oven. (Yield 510 mg, 92%).

Example 11

(Z)-4-Azido-1,3-dihydro-5-nitro-3-[(1H-pyrrol-2-yl)methylene]-2H-indol-2-one (J)

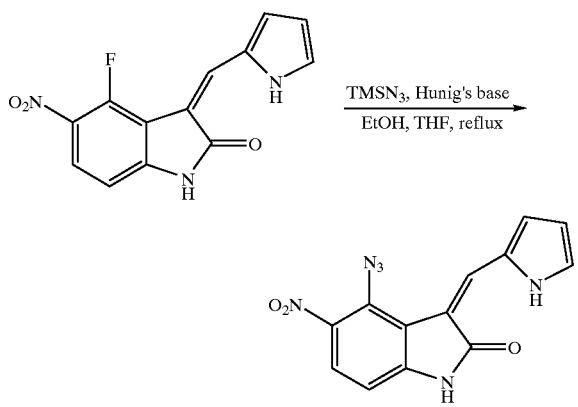

(Z)-1,3-Dihydro-4-fluoro-5-nitro-3-[(1H-pyrrol-2-yl)methylene]-2H-indol-2-one (400 mg, 1.46 mmol) (from Example 10) was suspended in THF/EtOH (20 mL/10 mL). Hunig's base (diisopropylethyl amine, 3.8 mL, 22 mmol) (Aldrich) and trimethylsilyl azide (1.87 mL, 14.65 mmol) (Aldrich) were successively added at r.t. The mixture was refluxed for 12 h. The homogeneous reaction mixture was cooled to r.t. and quenched with 1N HCl. The precipitate was collected by suction filtration, washed with water and dried in a vacuum oven to yield (Z)-4-azido-1,3-dihydro-5-nitro-3-[(1H-pyrrol-2-yl)methylene]-2H-indol-2-one as a red solid (Yield 340 mg, 79%).

Example 12

(Z)-4,5-Diamino-1,3-dihydro-3-[(1H-pyrrol-2-yl)methylene]-2H-indol-2-one (K)

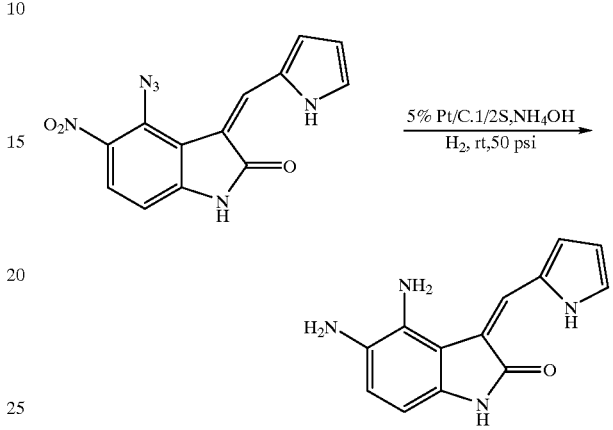

(Z)-4-Azido-1,3-dihydro-5-nitro-3-[(1H-pyrrol-2-yl)methylene]-2H-indol-2-one (340 mg, 1.15 mmol)(from Example 11) was dissolved in THF at rt (30 mL). Ammonium hydroxide was added (0.36 ml), followed by a catalytic amount of poisoned platinum on carbon (5% Pt/C•½S, 50 mg) (Engelhard Industries). The reaction mixture was hydrogenated in a Parr bomb under 50 psi of hydrogen for 2.5 h. The mixture was filtered through a cake of Celite®, and the cake was washed twice with THF. The hydrogenation was repeated with a fresh batch of catalyst, solvent and ammonium hydroxide (50 psi, 2 h). After filtration through Celite®, the mixture was concentrated under reduced pressure. The crude material was purified by flash chromatography on Silica Gel (230–400 mesh, eluted with 75% ethyl acetate in hexanes) to yield (Z)-4,5-diamino-1,3-dihydro-3-[(1H-pyrrol-2-yl)methylene]-2H-indol-2-one. (Yield 160 mg, 58%).

Example 13

(Z)-1,3-Dihydro-4-fluoro-3-[(3-methoxy-1H-pyrrol-2-yl)methylene]-5-nitro-2H-indol-2-one (L)

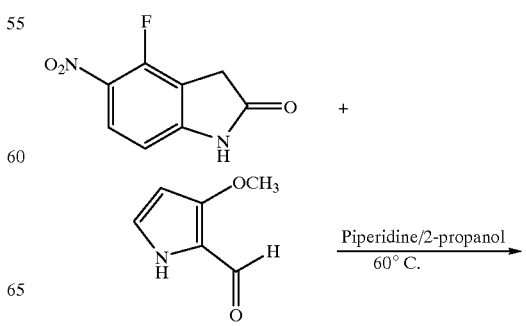

31
-continued

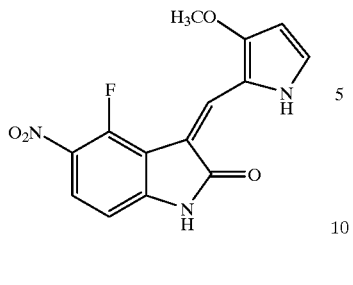

1,3-Dihydro-4-fluoro-5-nitro-2H-indol-2-one (5.25 g, 26.8 mmol) (Starting Material 9) was suspended in 110 mL solution of 1.35% piperidine in 2-propanol (Aldrich). 3-Methoxy-2-pyrrolecarboxaldehyde (3.68 g, 29.4 mmol, 1.1 eq.)(Bellamy, supra) was added and this mixture heated at 60° C. for 3.5 hours (TLC: 50% ethyl acetate in hexanes). The reaction mixture was poured into 1 L ice and water mixture and the solid precipitate filtered, washed with water and dried at 50° C. under high vacuum to give (Z)-1,3-dihydro-4-fluoro-3-[(3-methoxy-1H-pyrrol-2-yl)methylene]-5-nitro-2H-indol-2-one as an orange-brown solid. (Yield 6.6 g, 81%).

Example 14

(Z)-4-Azido-1,3-dihydro-3-[(3-methoxy-1H-pyrrol-2-yl)methylene]-5-nitro-2H-indol-2-one (M)

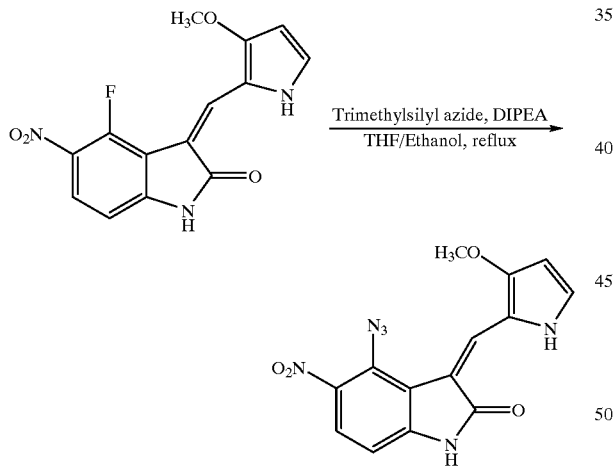

(Z)-1,3-Dihydro-4-fluoro-3-[(3-methoxy-1H-pyrrol-2-yl)methylene]-5-nitro-2H-indol-2-one (6.60 g, 21.8 mmol) (from Example 13) was suspended in 330 mL of THF and 165 mL of ethanol. To this mixture was added diisopropylethylamine (56.9ml, 326 mmol) and trimethylsilyl azide (28.6 mL, 218 mmol)(Aldrich). The reaction mixture was heated at reflux overnight, and then poured into 2 L mixture of ice and 1N HCl solution. The solid precipitate was filtered, washed with water and dried at 50° C. under high vacuum to give (Z)-4-azido-1,3-dihydro-3-[(3-methoxy-1H-pyrrol-2-yl)methylene]-5-nitro-2H-indol-2-one as a dark red solid. (Yield 6.44 g, 90%)

32
Example 15

(Z)-4,5-Diamino-1,3-dihydro-3-[(3-methoxy-1H-pyrrol-2-yl)methylene]-2H-indol-2-one (N)

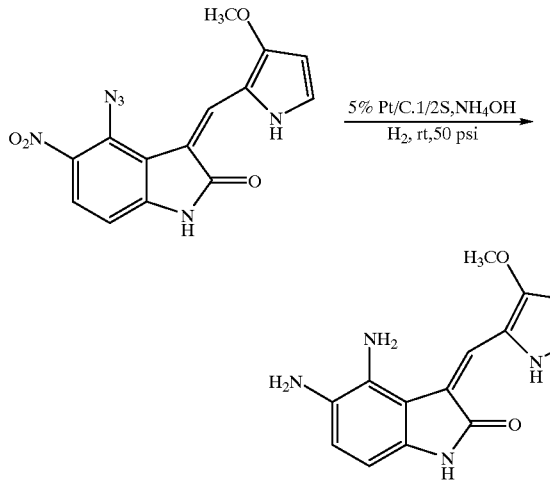

(Z)-4-Azido-1,3-dihydro-3-[(3-methoxy-1H-pyrrol-2-yl)methylene]-5-nitro-2H-indol-2-one (2.08 g, 6.37 mmol) (from Example 14) was dissolved in THF (160 mL) at r.t. Ammonium hydroxide was added (2 mL), followed by a catalytic amount of poisoned platinum on carbon (300 mg). The reaction mixture was hydrogenated in a Parr bomb under 50 psi of hydrogen for 12 h. The mixture was filtered through a cake of Celite®, the cake was washed twice with THF, and the filtrate was concentrated under reduced pressure. The crude material was purified by flash chromatography on Silica Gel (230–400 mesh, eluted with 75% ethyl acetate in hexanes) to yield (Z)-4,5-diamino-1,3-dihydro-3-[(3-methoxy-1H-pyrrol-2-yl)methylene]-2H-indol-2-one. (Yield 1.44 g, 84%).

Example 16

(Z)-2-Phenyl-8-[(1H-pyrrol-2-yl)methylene]-3,6,7,8-tetrahydro-pyrrolo[3,2-e]benzimidazol-7-one (O)

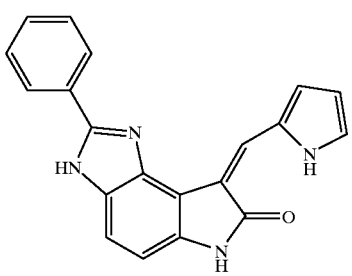

Using Method A above, (Z)-2-phenyl-8-[(1H-pyrrol-2-yl)methylene]-3,6,7,8-tetrahydro-pyrrolo[3,2-e]benzimidazol-7-one was prepared from the imidate of benzonitrile (220 mg, 0.88 mmol) (benzonitrile from Aldrich) and HBr. (Yield 58%).

Example 17

(Z)-8-[(3-Methoxy-1H-pyrrol-2-yl)methylene]-2-methyl-3,6,7,8-tetrahydro-pyrrolo-[3,2-e]benzimidazol-7-one (P)

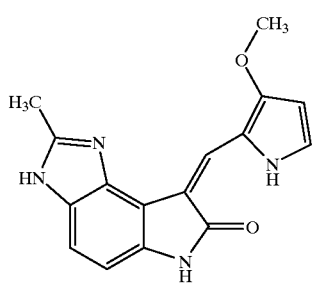

Using Method A above, (Z)-8-[(3-methoxy-1H-pyrrol-2-yl)methylene]-2-methyl-3,6,7,8-tetrahydro-pyrrolo-[3,2-e]benzimidazol-7-one was prepared from the imidate of acetonitrile (94.6 mg, 0.88 mmol) and HCl. (Yield 93%).

Example 18

(Z)-8-[(3-Methoxy-1H-pyrrol-2-yl)methylene]-2-phenyl-3,6,7,8-tetrahydro-pyrrolo[3,2-e]benzimidazol-7-one (Q)

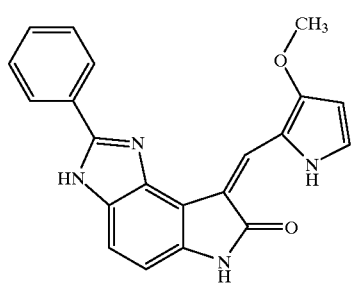

Using Method A above, (Z)-8-[(3-methoxy-1H-pyrrol-2-yl)methylene]-2-phenyl-3,6,7,8-tetrahydro-pyrrolo[3,2-e]benzimidazol-7-one was prepared from imidate of benzonitrile (165 mg, 0.88 mmol) and HCl. (Yield 58%).

Example 19

(Z)-4-[8-[(3-Methoxy-1H-pyrrol-2-yl)methylene]-3,6,7,8-tetrahydro-pyrrolo[3,2-e]-benzimidazol-2-yl]benzoic acid (R)

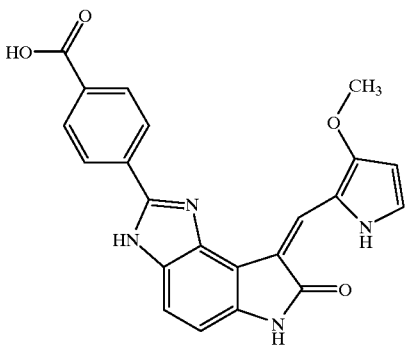

Using Method A above, (Z)-4-[8-[(3-methoxy-1H-pyrrol-2-yl)methylene]-3,6,7,8-tetrahydro-pyrrolo[3,2-e]-benzimidazol-2-yl]benzoic acid was prepared from imidate of 4-cyanobenzoic acid (191.5 mg, 0.88 mmol) and HCl. (Yield 82%).

Example 20

(Z)-2-(2-Hydroxyphenyl)-8-[(3-methoxy-1H-pyrrol-2-yl)methylene]-3,6,7,8-tetrahydro-pyrrolo[3,2-e]benzimidazol-7-one (S)

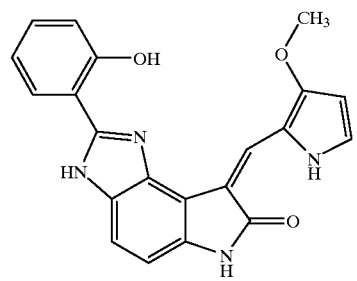

Using Method A above, (Z)-2-(2-hydroxyphenyl)-8-[(3-methoxy-1H-pyrrol-2-yl) methylene]-3,6,7,8-tetrahydro-pyrrolo[3,2-e]benzimidazol-7-one was prepared from imidate of 2-cyanophenol (166 mg, 0.88 mmol) and HCl. (Yield 78%).

Example 21

(Z)-2-[(4-Methoxyphenyl)methyl]-8-[(3-methoxy-1H-pyrrol-2-yl)methylene]-3,6,7,8-tetrahydro-pyrrolo[3,2-e]benzimidazol-7-one (T)

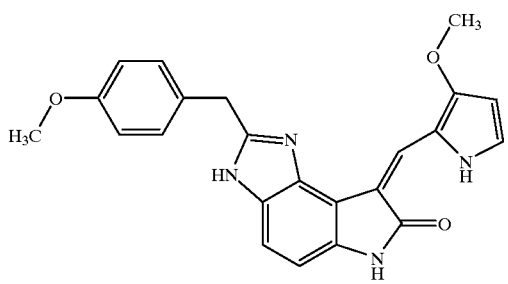

Using Method A above, (Z)-2-[(4-methoxyphenyl)methyl]-8-[(3-methoxy-1H-pyrrol-2-yl)methylene]-3,6,7,8-tetrahydro-pyrrolo[3,2-e]benzimidazol-7-one was prepared from the imidate of (4-methoxyphenyl)-acetonitrile (191.5 mg, 0.88 mmol) and HCL. (Yield 97%).

Example 22 rac-(Z)-2-(1-Hydroxy-1-phenyl-methyl)-8-[(3-methoxy-1H-pyrrol-2-yl)methylene]-3,6,7,8-tetrahydro-pyrrolo[3,2-e]benzimidazol-7-one (U)

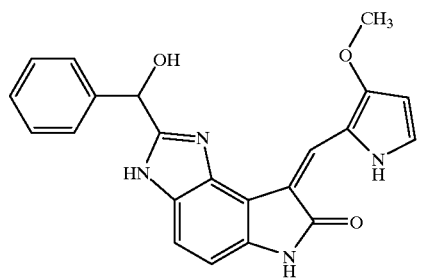

Using Method A above, rac-(Z)-2-(1-hydroxy-1-phenyl-methyl)-8-[(3-methoxy-1H-pyrrol-2-yl)methylene]-3,6,7,8-tetrahydro-pyrrolo[3,2-e]benzimidazol-7-one was prepared from the imidate of mandelonitrile (179 mg, 0.88 mmol) and HCl. (Yield 50%).

Example 23

(Z)-2-[2-(4-Hydroxyphenyl)ethyl]-8-[(3-methoxy-1H-pyrrol-2-yl)methylene]-3,6,7,8-tetrahydro-pyrrolo[3,2-e]benzimidazol-7-one (V)

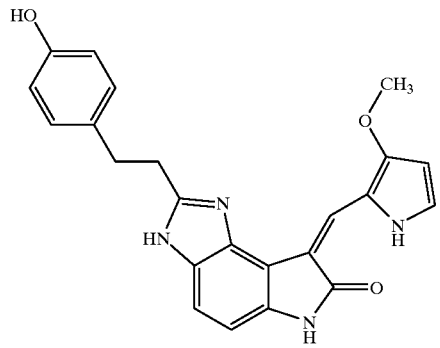

Using Method A above, (Z)-2-[2-(4-hydroxyphenyl)ethyl]-8-[(3-methoxy-1H-prepared from imidate of 3-(4-hydroxyphenyl)-propionitrile (191.5 mg, 0.88 mmol) and HCl. (Yield 79%).

Example 24

(Z)-2-[3-(Phenyl)propyl]-8-[(3-methoxy-1H-pyrrol-2-yl)methylene]-3,6,7,8-tetrahydro-pyrrolo[3,2-e]benzimidazol-7-one (W)

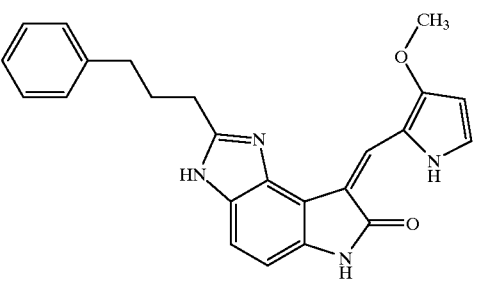

Using Method A above, (Z)-2-[3-(phenyl)propyl]-8-[(3-methoxy-1H-pyrrol-2-yl)methylene]-3,6,7,8-tetrahydro-pyrrolo[3,2-e]benzimidazol-7-one was prepared from the imidate of 4-phenylbutyronitrile (189.8 mg, 0.88 mmol) and HCl. (Yield 82%).

Example 25

(Z)-2-[N-(3-Methoxypropyl)amino]-8-[(3-methoxy-1H-pyrrol-2-yl)methylene]-3,6,7,8-tetrahydro-pyrrolo[3,2-e]benzimidazol-7-one (X)

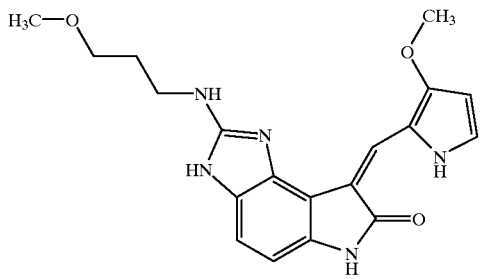

Using Method B above (Step 2), (Z)-2-[N-(3-methoxypropyl)amino]-8-[(3-methoxy-1H-pyrrol-2-yl)methylene]-3,6,7,8-tetrahydro-pyrrolo[3,2-e]benzimidazol-7-one was prepared from 3-methoxypropyl isothiocyanate (150 μL) (Lancaster). (Yield 23%).

Example 26

(Z)-2-[N-(3,4-Dimethoxyphenyl)amino]-8-[(3-methoxy-1H-pyrrol-2-yl)methylene]-3,6,7,8-tetrahydro-pyrrolo[3,2-e]benzimidazol-7-one (Y)

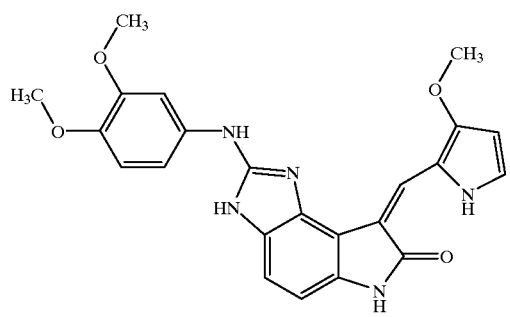

Using Method B above (Step 2), (Z)-2-[N-(3,4-dimethoxyphenyl)amino]-8-[(3-methoxy-1H-pyrrol-2-yl)methylene]-3,6,7,8-tetrahydro-pyrrolo[3,2-e]benzimidazol-7-one was prepared from 3,4-dimethoxyphenyl isothiocyanate (214.8 mg) (Transworld). (Yield 84%).

Example 27

(Z)-2-[N-(4-Methoxyphenyl)amino]-8-[(3-methoxy-1H-pyrrol-2-yl)methylene]-3,6,7,8-tetrahydro-pyrrolo[3,2-e]benzimidazol-7-one (Z)

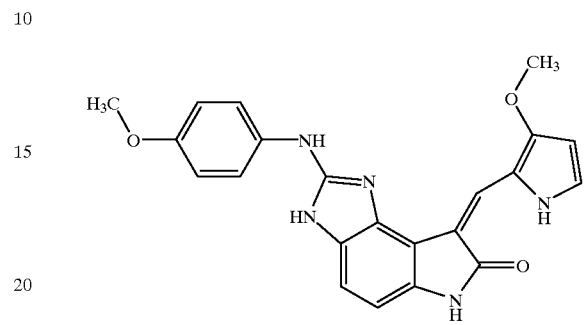

Using Method B above (step 1), (Z)-2-[N-(4-methoxyphenyl)amino]-8-[(3-methoxy-1H-pyrrol-2-yl)methylene]-3,6,7,8-tetrahydro-pyrrolo[3,2-e]benzimidazol-7-one was prepared from 4-methoxyphenyl isothiocyanate (182 μL) (Transworld). (Yield 32%).

Example 28

(Z)-2-[N-[(4-Methoxyphenyl)methyl]amino]-8-[(3-methoxy-1H-pyrrol-2-yl)methylene]-3,6,7,8-tetrahydro-pyrrolo[3,2-e]benzimidazol-7-one (AA)

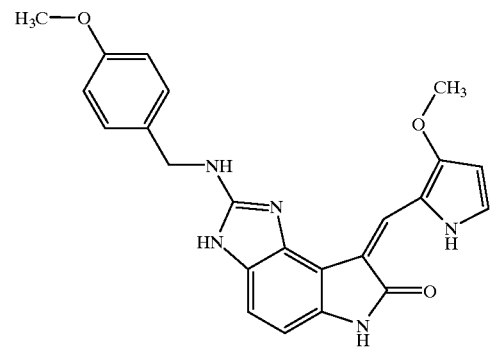

Using Method B (Step 1) above, (Z)-2-[N-[(4-methoxyphenyl)methyl]amino]-8-[(3-methoxy-1H-pyrrol-2-yl)methylene]-3,6,7,8-tetrahydro-pyrrolo[3,2-e]benzimidazol-7-one was prepared from 4-methoxybenzyl isothiocyanate (197 μL) (Transworld) (Yield 38%).

Example 29

(Z)-2-[N-(3-Acetylphenyl)amino]-8-[(3-methoxy-1H-pyrrol-2-yl)methylene]-3,6,7,8-tetrahydro-pyrrolo[3,2-e]benzimidazol-7-one (BB)

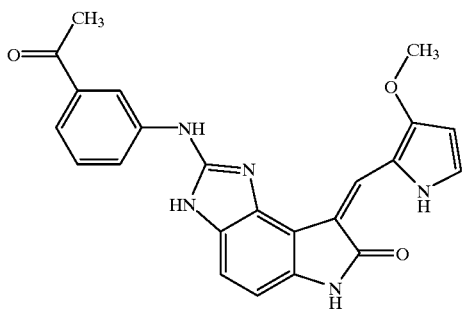

Using Method B (Step 1) above, (Z)-2-[N-(3-acetylphenyl)amino]-8-[(3-methoxy-1H-pyrrol-2-yl)methylene]-3,6,7,8-tetrahydro-pyrrolo[3,2-e]benzimidazol-7-one was prepared from 3-acetylphenyl isothiocyanate (195 mg) (Transworld). (Yield 76%).

Example 30

(Z)-4-[[8-[(3-Methoxy-1H-pyrrol-2-yl)methylene]-7-oxo-3,6,7,8-tetrahydro-imidazo[4,5-e]indol-2-yl]amino]-benzoic acid ethyl ester (CC)

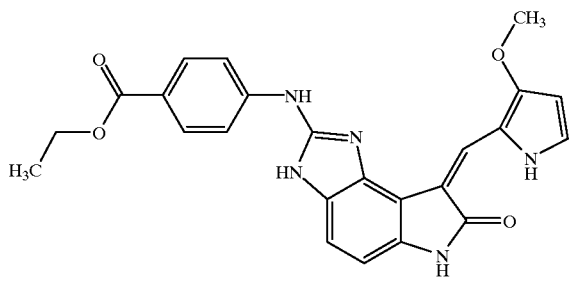

Using Method B (Step 1) above, (Z)-4-[[8-[(3-methoxy-1H-pyrrol-2-yl)methylene]-7-oxo-3,6,7,8-tetrahydro-imidazo[4,5-e]indol-2-yl]amino]-benzoic acid ethyl ester was prepared from 4-ethoxycarbonylphenyl isothiocyanate (228 mg) (Transworld). (Yield 99%).

Example 31

(Z)-2-[N-(4-Dimethylaminophenyl)amino]-8-[(3-methoxy-1H-pyrrol-2-yl)methylene]-3,6,7,8-tetrahydro-pyrrolo[3,2-e]benzimidazol-7-one (DD)

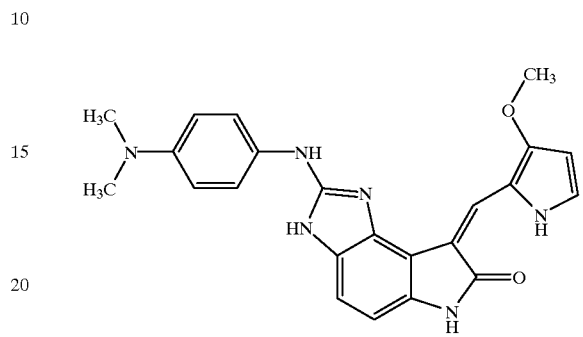

Using Method B (Step 1) above, (Z)-2-[N-(4-dimethylaminophenyl)amino]-8-[(3-methoxy-1H-pyrrol-2-yl)methylene]-3,6,7,8-tetrahydro-pyrrolo[3,2-e]benzimidazol-7-one was prepared from 4-dimethylaminophenyl isothiocyanate (196 mg) (Transworld). (Yield 76%).

Example 32

(Z)-4-[[8-[(3-Methoxy-1H-pyrrol-2-yl)methylene]-7-oxo-3,6,7,8-tetrahydro-imidazo[4,5-e]indol-2-yl]amino]-benzoic acid methyl ester (EE)

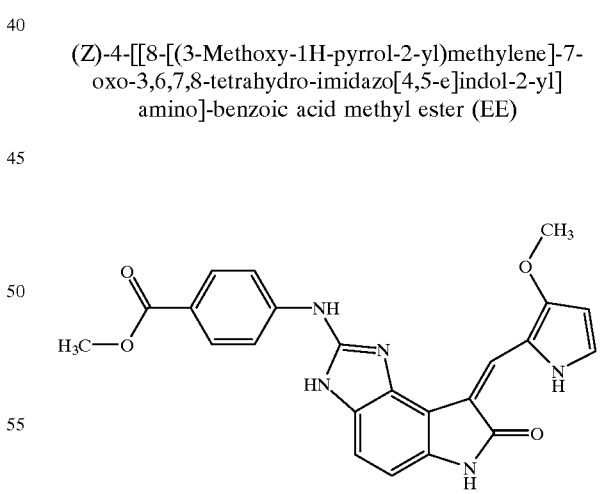

Using Method B (Step 1) above, (Z)-4-[[8-[(3-methoxy-1H-pyrrol-2-yl)methylene]-7-oxo-3,6,7,8-tetrahydro-imidazo[4, 5-e]indol-2-yl]amino]-benzoic acid methyl ester was prepared from 4-methoxycarbonylphenyl isothiocyanate (212 mg) (TransworLd). (Yield 75%).

Example 33

(Z)-2-[N-[(4-Fluorophenyl)methyl]amino]-8-[(3-methoxy-1H-pyrrol-2-yl)methylene]-3,6,7,8-tetrahydro-pyrrolo[3,2-e]benzimidazol-7-one (FF)

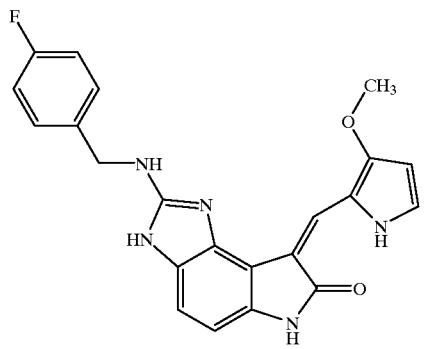

Using Method B (Step 1) above, (Z)-2-[N-[(4-fluorophenyl)methyl]amino]-8-[(3-methoxy-1H-pyrrol-2-yl)methylene]-3,6,7,8-tetrahydro-pyrrolo[3,2-e]benzimidazol-7-one was prepared from 4-fluorobenzyl isothiocyanate (184 μL) (Transworld). (Yield 59%).

Example 34

(Z)-2-[N-[2-(3,4-Dimethoxyphenyl)ethyl]amino]-8-[(3-methoxy-1H-pyrrol-2-yl)methylene]-3,6,7,8-tetrahydro-pyrrolo[3,2-e]benzimidazol-7-one (GG)

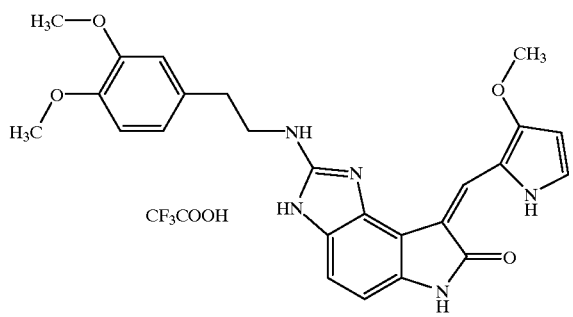

Using Method B (Step 1) above, (Z)-2-[N-[2-(3,4-dimethoxyphenyl)ethyl]amino]-8-[(3-methoxy-1H-pyrrol-2-yl)methylene]-3,6,7,8-tetrahydro-pyrrolo[3,2-e]benzimidazol-7-one was prepared from 2-(3,4-dimethoxyphenyl)-ethyl isothiocyanate (246 μL) (Transworld). (Yield 78%).

Example 35 rac-(Z)-8-[(3-Methoxy-1H-pyrrol-2-yl)methylene]-2-[N-(1-phenylethyl)amino]-3,6,7,8-tetrahydro-pyrrolo[3,2-e]benzimidazol-7-one (HH)

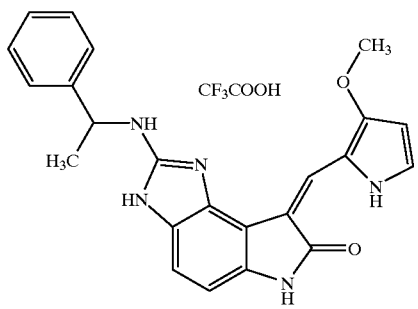

Using Method B (Step 1) above, rac-(Z)-8-[(3-methoxy-1H-pyrrol-2-yl) methylene]-2-[N-(1-phenylethyl)amino]-3,6,7,8-tetrahydro-pyrrolo[3,2-e]benzimidazol-7-one was prepared from alpha-methylbenzyl isothiocyanate (180 μL) (Transworld). (Yield 31%).

Example 36

(Z)-2-[N-(2-Methoxyphenyl)amino]-8-[(3-methoxy-1H-pyrrol-2-yl) methylene]-3,6,7,8-tetrahydro-pyrrolo[3,2-e]benzimidazol-7-one (II)

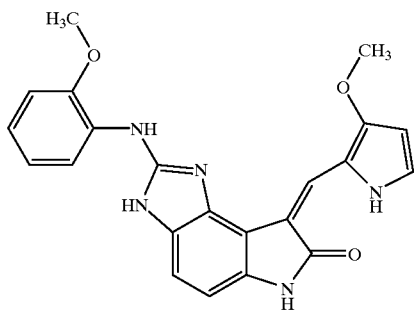

Using Method B (Step 1) above, (Z)-2-[N-(2-methoxyphenyl)amino]-8-[(3-methoxy-1H-pyrrol-2-yl) methylene]-3,6,7,8-tetrahydro-pyrrolo[3,2-e]benzimidazol-7-one was prepared from 2-methoxyphenyl isothiocyanate (182 μL) (Transworld). (Yield 37%).

Example 37

(Z)-8-[(3-Methoxy-1H-pyrrol-2-yl)methylene]-2-[N-(4-phenylbutyl)amino]-3,6,7,8-tetrahydro-pyrrolo[3,2-e]benzimidazol-7-one (JJ)

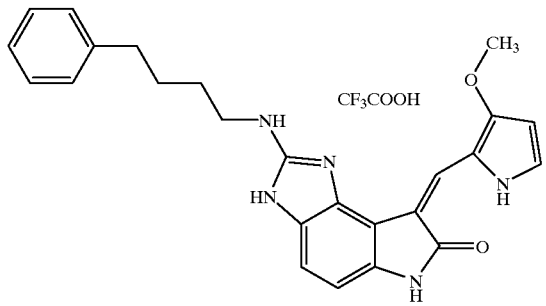

Using Method B (Step 1) above, (Z)-8-[(3-methoxy-1H-pyrrol-2-yl)methylene]-2-[N-(4-phenylbutyl)amino]-3,6,7,8-tetrahydro-pyrrolo[3,2-e]benzimidazol-7-one was prepared from 4-phenylbutyl isothiocyanate (210 mg) (Sigma). (Yield 52%).

Example 38

(Z)-8-[(3-Methoxy-1H-pyrrol-2-yl)methylene]-2-[N-[(2-tetrahydrofuranyl)methyl]-amino]-3,6,7,8-tetrahydro-pyrrolo[3,2-e]benzimidazol-7-one (KK)

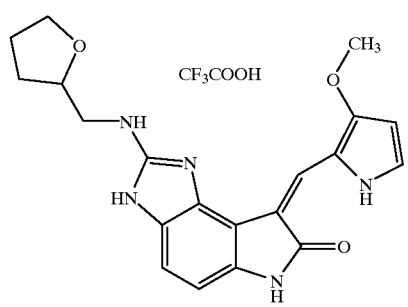

Using Method B (Step 1) above, (Z)-8-[(3-methoxy-1H-pyrrol-2-yl)methylene]-2-[N-[(2-tetrahydrofuranyl)methyl]-amino]-3,6,7,8-tetrahydro-pyrrolo[3,2-e]benzimidazol-7-one was prepared from 2-tetrahydrofurfuryl isothiocyanate (157 mg) (Transworld). (Yield 44%).

Example 39

(Z)-4-[[8-[(3-Methoxy-1H-pyrrol-2-yl)methylene]-7-oxo-3,6,7,8-tetrahydro-imidazo[4,5-e]indol-2-yl]amino]-butanoic acid ethyl ester (LL)

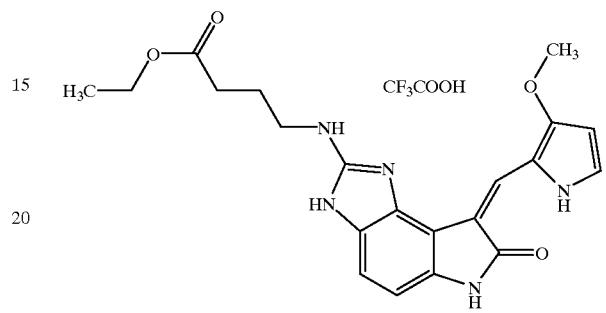

Using Method B (Step 1) above, (Z)-4-[[(3-methoxy-1H-pyrrol-2-yl)methylene]-7-3,6,7,8-tetrahydro-imidazo-[4,5-e]indol-2yl]amino]-butanoic acid ethyl ester was prepared from ethyl isothiocyanato-butyrate (191 μL) (Transworld). (Yield 35%).

Example 40

(Z)-8-[(3-Methoxy-1H-pyrrol-2-yl)methylene]-2-[N-(1-naphthyl) amino]-3,6,7,8-tetrahydro-pyrrolo[3,2-e]benzimidazol-7-one (MM)

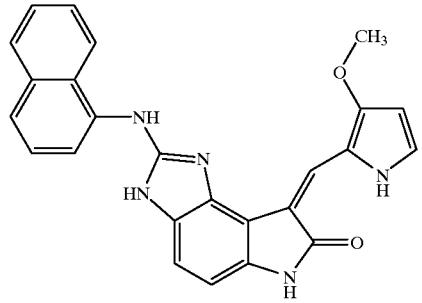

Using Method B (Step 1) above, (Z)-8-[(3-methoxy-1H-pyrrol-2-yl)methylene]-2-[N-(1-naphthyl)amino]-3,6,7,8-tetrahydro-pyrrolo[3,2-e]benzimidazol-7-one was prepared from 1-naphthyl isothiocyanate (204 mg) (Aldrich). (Yield 65%).

Example 41

(Z)-8-[(3-Methoxy-1H-pyrrol-2-yl)methylene]-2-[N-[2-(N-piperidinyl)ethyl]-amino]-3,6,7,8-tetrahydro-pyrrolo[3,2-e]benzimidazol-7-one (NN)

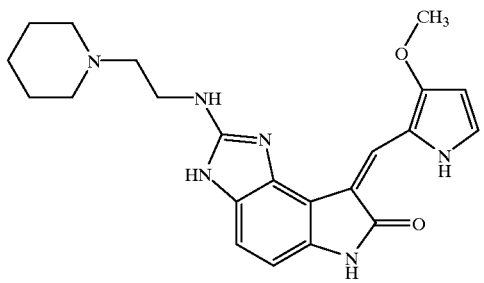

Using Method B (Step 1) above, (Z)-8-[(3-methoxy-1H-pyrrol-2-yl)methylene]-2-[N-[2-(N-piperidinyl)ethyl]-amino]-3,6,7,8-tetrahydro-pyrrolo[3,2-e]benzimidazol-7-one was prepared from 2-piperidinoethyl isothiocyanate (187 mg) (Transworld). (Yield 68%).

Example 42

(Z)-1,3-Dihydro-4-fluoro-3-[(4-methyl-1H-imidazol-5-yl)methylene]-5-nitro-2H-indol-2-one (OO)

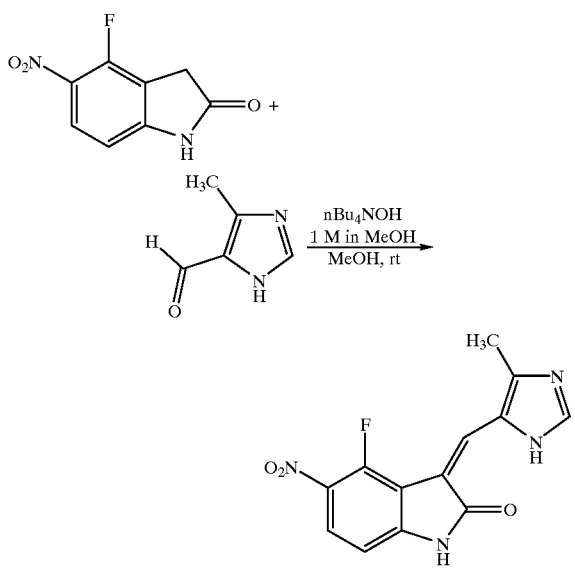

To a solution of 1,3-dihydro-4-fluoro-5-nitro-2H-indol-2-one (1 g, 5 mmol) in MEOH (10 mL) (Starting Material 10), was successively added, at r.t., 4-methyl-5-imidazolecarboxaldehyde (612 mg, 5.5 mmol) (Aldrich) and tetrabutyl ammonium hydroxide (11 mL, 1.0 M solution in MeOH)(Aldrich). The mixture was stirred at r.t. for 4 h. The resulting greenish precipitate was collected by suction filtration, washed with ether and air dried to yield (Z)-1,3-dihydro-4-fluoro-3-[(4-methyl-1H-imidazol-5-yl)methylene]-5-nitro-2-indol-2-one as a green powder. (Yield 1.14 g, 79%).

Example 43

(Z)-4-Azido-1,3-dihydro-3-[(4-methyl-1H-imidazol-5-yl)methylene]-5-nitro-2H-indol-2-one (PP)

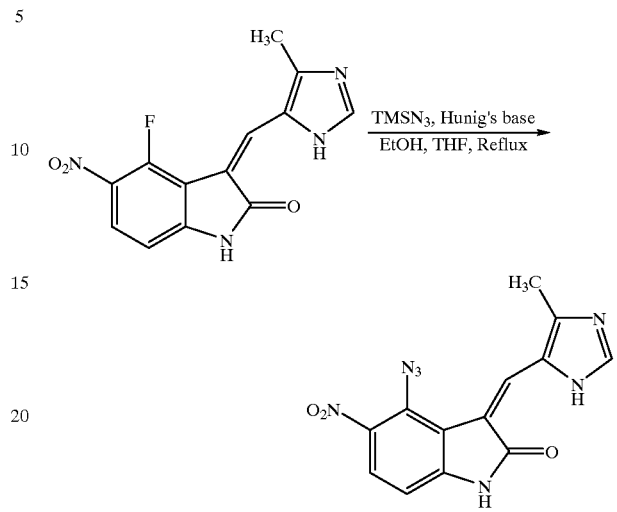

(Z)-1,3-Dihydro-4-fluoro-3-[(4-methyl-1H-imidazol-5-yl)methylene]-5-nitro-2H-indol-2-one (576 mg, 2.0 mmol) (from Example 42 above) was suspended in THF/EtOH (15 mL/8 mL). Hunig's base (diisopropylethyl amine, 5 mL, 30 mmol) (Aldrich) and trimethylsilyl azide (2.6 mL, 20 mmol) (Aldrich) were successively added at r.t. The mixture was heated at reflux for 3 h 20 min. The heterogeneous reaction mixture was cooled to r.t. and the orange suspension was collected by suction filtration. The precipitate was washed with ethanol and dried in a vacuum oven overnight. (Yield 490 mg, 79%).

Example 44

(Z)-4-Amino-1,3-dihydro-3-[(4-methyl-1H-imidazol-5-yl)methylene]-5-nitro-2H-indol-2-one (QQ)

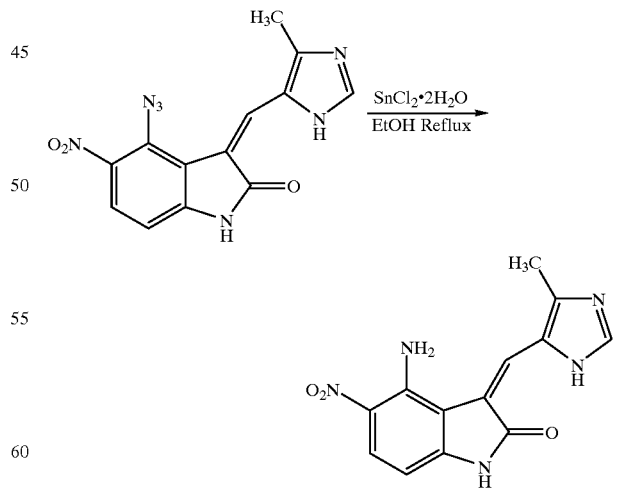

To a suspension of (Z)-4-azido-1,3-dihydro-3-[(4-methyl-1H-imidazol-5-yl)methylene]-5-nitro-2H-indol-2-one (160 mg, 0.51 mmol) (from Example 43 above) in EtOH (10 mL), was added, at r.t., tin dichloride dihydrate. The heterogeneous mixture was heated at reflux for 6 h then cooled to r.t. The orange solid was collected by suction filtration, washed with ether and dried in a vacuum oven overnight to yield (Z)-4-amino-1,3-dihydro-3-[(4-methyl-1H-imidazol-5-yl) methylene]-5-nitro-2H-indol-2-one. (Yield 45 mg, 31%).

Example 45

(Z)-4,5-Diamino-1,3-dihydro-3-[(4-methyl-1H-imidazol-5-yl)methylene]-2H-indol-2-one (RR)

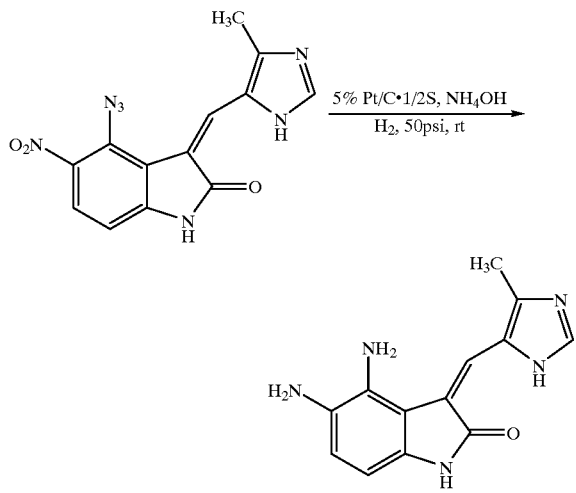

(Z)-4-azido-1,3-dihydro-3-[(4-methyl-1H-imidazol-5-yl) methylene]-5-nitro-2H-indol-2-one (150 mg, 0.48 mmol) (from Example 44 above) was suspended in THF (40 mL) at r.t. Ammonium hydroxide was added (0.15 mL), followed by a catalytic amount of poisoned platinum on carbon (50 mg, 5% Pt/C•½S) (Engelhard Ind.). The reaction mixture was hydrogenated in a Parr bomb under 50 psi of hydrogen for 16 h. The mixture was filtered through a cake of Celite®, and the cake was washed twice with THF. The crude material was purified by flash chromatography on Silica Gel (230–400 mesh, eluted with 1% MeOH/1% ET$_3$N in THF) to afford (Z)-4,5-diamino-1,3-dihydro-3-[(4-methyl-1H-imidazol-5-yl)methylene]-2H-indol-2-one as a dark red solid. (Yield 52 mg, 42%).

Example 46

(Z)-8-[(4-Methyl-1H-imidazol-5-yl)methylene]-3,6,7,8-tetrahydro-pyrrolo[3,2-e]benzimidazol-7-one (SS)

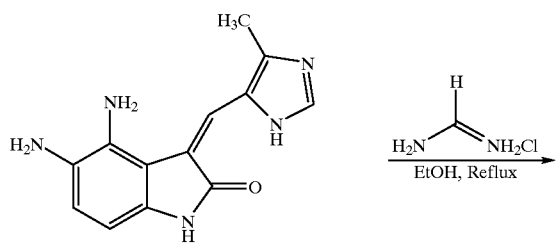

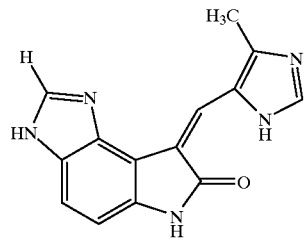

A mixture of (Z)-4,5-diamino-1,3-dihydro-3-[(4-methyl-1H-imidazol-5-yl)methylene]-2H-indol-2-one (30 mg, 0.1175 mmol) (from Example 45 above) and formamidine hydrochloride (95 mg, 1.18 mmol) (Aldrich) in ethanol (1.5 mL) was heated at reflux for 1 h. The mixture was cooled to r.t., and the reaction was quenched with water. The aqueous layer was extracted with dichloromethane. The combined organic layers were washed with brine, dried over anhydrous Mg$_2$SO$_4$ and concentrated under reduced pressure. The crude oily residue was triturated with ether and the resulting yellow precipitate was collected by suction filtration. (First crop; yield 5 mg, 16%).

Example 47

(Z)-8-[(3-Methoxy-1H-pyrrol-2-yl)methylene]-3,6,7,8-tetrahydro-pyrrolo-[3,2-e]benzimidazol-7-one (TT)

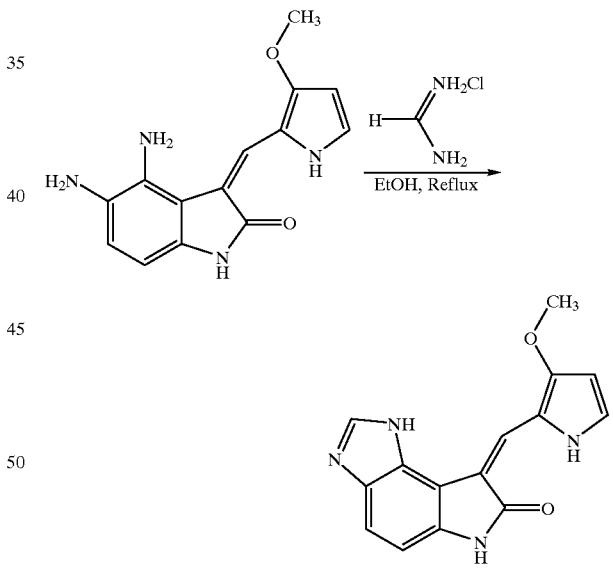

A mixture of (Z)-4,5-diamino-1,3-dihydro-3-[(3-methoxy-1H-pyrrol-2-yl) methylene]-2H-indol-2-one (60 mg, 0.22 mmol) (from Example 15 above) and formamidine hydrochloride (177 mg, 2.2 mmol) (Aldrich) in ethanol (3 mL) was heated at reflux for 45 min. The mixture was cooled to room temperature, and water was slowly added to induce precipitation. The precipitate was collected by suction filtration, washed with water and dried in a vacuum oven overnight to give (Z)-8-[(3-methoxy-1H-pyrrol-2-yl) methylene]-3,6,7,8-tetrahydro-pyrrolo-[3,2-e] benzimidazol-7-one. (Yield 48 mg, 99%).

Example 48

(Z)-8-[(3-Methoxy-1H-pyrrol-2-yl)methylene]-2-[N-[4-phenyl-(2-methoxyphenyl)]amino]-3,6,7,8-tetrahydro-pyrrolo[3,2-e]benzimidazol-7-one (UU)

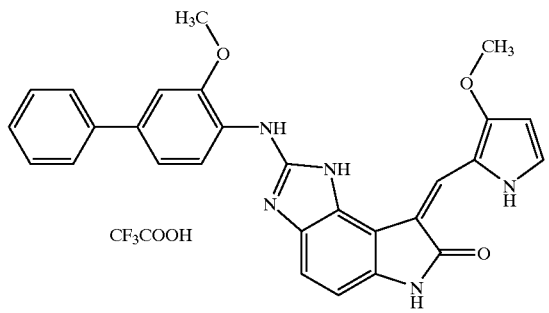

Using Method B above (Step 1), (Z)-8-[(3-methoxy-1H-pyrrol-2-yl)methylene]-2-[N-[4-phenyl-(2-methoxyphenyl)]amino]-3,6,7,8-tetrahydro-pyrrolo[3,2-e]benzimidazol-7-one was prepared from [4-phenyl-(2-methoxyphenyl)] isothiocyanate (265 mg) (Transworld). (Yield 102 mg, 96%).

Example 49

(Z)-2-[N-(1,3-Benzodioxol-5-yl)methylamino]-8-[(3-methoxy-1H-pyrrol-2-yl)methylene]-3,6,7,8-tetrahydro-pyrrolo[3,2-e]benzimidazol-7-one (VV)

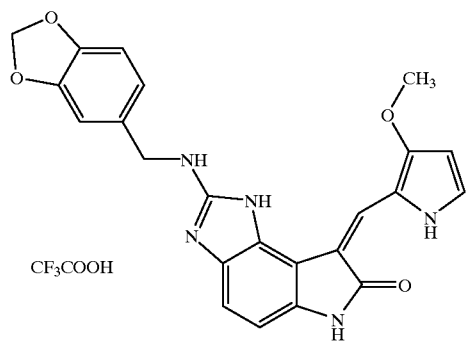

Using Method B above (Step 2), (Z)-2-[N-(1,3-benzodioxol-5-yl)methylamino]-8-[(3-methoxy-1H-pyrrol-2-yl)methylene]-3,6,7,8-tetrahydro-pyrrolo[3,2-e]benzimidazol-7-one was prepared from (1,3-benzodioxol-5-yl)methylisothiocyanate (212 mg) (Transworld). (Yield 86 mg, 90%).

Example 50

(Z)-8-[(3-Methoxy-1H-pyrrol-2-yl)methylene]-2-[N-(1-naphthalenyl)methylamino]-3,6,7,8-tetrahydro-pyrrolo[3,2-e]benzimidazol-7-one (WW)

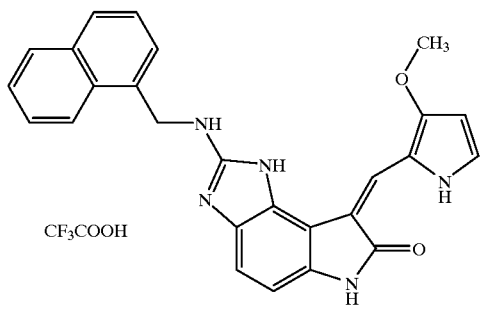

Using Method B above (Step 2), (Z)-8-[(3-methoxy-1H-pyrrol-2-yl)methylene]-2-[N-(1-naphthalenyl)methylamino]-3,6,7,8-tetrahydro-pyrrolo[3,2-e]benzimidazol-7-one was prepared from (1-naphthalenyl)methylisothiocyanate (220 mg) (Transworld). (Yield 60 mg, 62%).

Example 51

(Z)-8-[(3-Methoxy-1H-pyrrol-2-yl)methylene]-2-[N-(3-phenylpropyl)amino]-3,6,7,8-tetrahydro-pyrrolo[3,2-e]benzimidazol-7-one (XX)

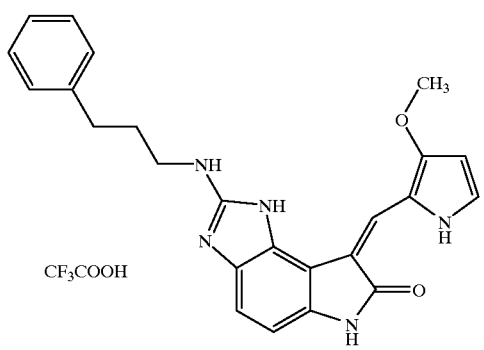

Using Method B above (Step 2), (Z)-8-[(3-methoxy-1H-pyrrol-2-yl)methylene]-2-[N-(3-phenylpropyl)amino]-3,6,7,8-tetrahydro-pyrrolo[3,2-e]benzimidazol-7-one was prepared from 3-phenylpropylisothiocyanate (195 mg) (Transworld). (Yield 44 mg, 48%).

Example 52

(Z)-2-[N-(2,3-Dihydro-1H-inden-5-yl)amino]-8-[(3-methoxy-1H-pyrrol-2-yl)methylene]-3,6,7,8-tetrahydro-pyrrolo[3,2-e]benzimidazol-7-one (YY)

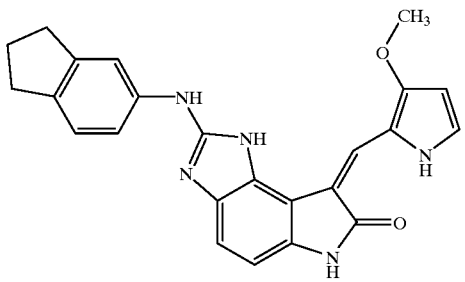

Using Method B above (Step 2), (Z)-2-[N-(2,3-dihydro-1H-inden-5-yl)amino]-8-[(3-methoxy-1H-pyrrol-2-yl)methylene]-3,6,7,8-tetrahydro-pyrrolo[3,2-e] benzimidazol-7-one was prepared from (2,3-dihydro-1H-inden-5-yl) isothiocyanate (193 mg) (Transworld). (Yield 27 mg, 30%).

Example 53

Antiproliferative Activity

The antiproliferative activity of the compounds of the invention is demonstrated below. These effects indicate that the compounds of the present invention are useful in treating cancer, in particular solid tumors such as breast and colon tumors.

CDK2 FlashPlate Assay

To determine inhibition of CDK2 activity, purified recombinant retinoblastoma (Rb) protein was coated on 96 well FlashPlates (New England Nuclear, Boston, Mass.). Rb is a natural substrate for phosphorylation by CDK2 (Herwig and Strauss *Eurr. J. Biochem.*, Vol. 246 (1997) pp. 581–601 and references therein). Recombinant active human Cyclin E/CDK2 complexes were partially purified from extracts of insect cells. The active Cyclin E/CDK2 was added to the Rb-coated FlashPlates along with $^{33}$P-ATP and dilutions of test compounds. Plates were incubated for 25 minutes at room temperature with shaking, then washed and counted in the Topcount scintillation counter (Packard Instrument Co., Downers Grove, Ill.). Dilutions of test compounds were tested in duplicate in each assay. The percent inhibition of Rb phosphorylation, which is a measure of the inhibition of CDK2 activity, was determined according to the following formula:

$$100 \times \left[ 1 - \frac{\text{test compound} - \text{nonspecific}}{\text{total} - \text{nonspecific}} \right]$$

where "test compound" refers to the average counts per minute of the test duplicates, "nonspecific" refers to the average counts per minute when no Cyclin E/CDK2 was added, and "total" refers to the average counts per minute when no compound was added.

The results of the foregoing in vitro experiments are set forth in Table I below.

TABLE I

| [001b] Compound | CDK2 IC$_{50}$ (μM) |
|---|---|
| OO | <3.5 |
| PP | <3.5 |
| QQ | <3.5 |
| RR | <3.5 |
| SS | <3.5 |
| O | <3.5 |
| TT | <3.5 |
| P | <3.5 |
| Q | <3.5 |
| R | <3.5 |
| S | <3.5 |
| T | <3.5 |
| V | <3.5 |
| W | <3.5 |
| X | <3.5 |
| U | <3.5 |
| DD | <3.5 |
| HH | <3.5 |
| KK | <3.5 |

| | CDK2 | |
|---|---|---|
| Compound | % Inhibition | Concentration (μM) |
| Y | <50% | 0.5 |
| Z | <50% | 0.5 |
| AA | >50% | 0.5 |
| BB | <50% | 0.5 |
| VV | <50% | 0.5 |
| CC | <50% | 0.5 |
| EE | <50% | 0.5 |
| FF | >50% | 0.5 |
| GG | <50% | 0.5 |
| II | <50% | 0.5 |
| JJ | <50% | 0.5 |
| WW | <50% | 0.5 |
| XX | <50% | 0.5 |
| LL | >50% | 0.5 |
| MM | >50% | 0.5 |
| NN | >50% | 0.5 |
| YY | <50% | 0.5 |

Cell-Based Assays

The estrogen receptor negative epithelial breast carcinoma Line (MDA-MB-435) was purchased from American Type Cell Culture Collection (ATCC; Rockville, Md.) and was grown in the medium recommended by ATCC. For analysis of the effect of the test compounds on growth of these cells, the cells were plated at 2000 cells per well in a 96-well tissue culture plate, and were incubated overnight at 37°C with 5% CO$_2$. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 μM. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below.

3-(4, 5-Dimethylthiazole-2-yl)-2,5-diphenyl-2H-tetrazolium bromide (thiazolyl blue; MTT) was added to each well to yield a final concentration of 1 mg/ml. The plates were then incubated at 37°C for 3 hours. The plates were centrifuged at 1000 rpm for 5 minutes prior to aspiration of the MTT-containing medium. The MTT-containing medium was then removed and 100 μl 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the absorbance of the blank (no cell) wells from all wells, then subtracting the division of the average absorbance of each test duplicate by the average of the controls from 1.00. Inhibitory concentrations ($IC_{50}$) were determined from the linear regression of a plot of the logarithm of the concentration versus the percent inhibition.

The colon carcinoma line SW480 also was obtained from the ATCC and was tested according to the same protocol provided above with the following modification: cell line SW480 was plated at 1000 cells per well and analyzed at 4 days post addition of test compound.

The results of the foregoing in vitro tests are set forth below in Tables II and III.

TABLE II

Antiproliferative Activity In Cell Line MDA-MB435*

| Compound | MDA-MB435 $IC_{50}$ ($\mu$M) |
|---|---|
| P | <3.5 |
| SS | <3.5 |

*Most of the data reflect the results of one experiment. In those cases where an experiment was repeated, the above data is an average of the results of the separate experiments.

TABLE III

Antiproliferative Activity In Cell Line SW480

| Compound | SW480 $IC_{50}$ ($\mu$M) |
|---|---|
| P | <1.0 |

Example 54

Tablet Formulation

| Item | Ingredients | mg/Tablet | | | | | |
|---|---|---|---|---|---|---|---|
| 1 | Compound 1* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound 1 represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50°C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 55

Capsule Formulation

| Item | Ingredients | mg/Capsule | | | | |
|---|---|---|---|---|---|---|
| 1 | Compound 1* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound 1 represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 56

Injection Solution/Emulsion Preparation

| Item | Ingredient | mg/mL |
|---|---|---|
| 1 | Compound 1* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound 1 represents a compound of the invention.

Manufacturing Procedure:
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

Example 57

Injection Solution/Emulsion Preparation

| Item | Ingredient | mg/mL |
|---|---|---|
| 1 | Compound 1* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure:
1. Dissolve item 1 in item 2
2. Add items 3, 4 and 5 to item 6 and mix until dispersed, then homogenize.

What is claimed is:

1. A compound of formula

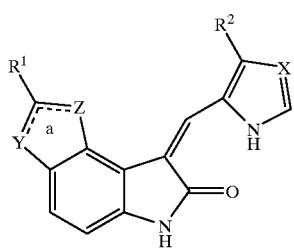

I or a pharmaceutically acceptable salt of the foregoing compound, wherein $R^1$ is selected from the group consisting of
—H,
—$OR^3$,
—$COR^3$,
—$COOR^3$,
—$CONR^4R^5$,
—$NR^4R^5$,
lower alkyl which optionally may be substituted by the group consisting of —$OR^3$, —$NR^4R^5$, halogen, —$COR^3$, —$COOR^3$, —$OCOR^3$, —$CONR^4R^5$, —CN, —$SO_2R^3$, —$SO_2NR^4R^5$, cycloalkyl, heterocycle, aryl, and heteroaryl, wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^3$, —$NR^4R^5$, halogen, —$COR^3$, —$COOR^3$, —$OCOR^3$, —$OCOR^3$, —$CONR^4R^5$, —CN, —$SO_2R^3$, —$SO_2NR^4R^5$, lower alkyl, heterocycle, aryl, and heteroaryl, wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^3$, —$NR^4R^5$, halogen, —$COR^3$, —$COOR^3$, —$OCOR^3$, —$CONR^4R^5$, —CN, —$SO_2R^3$, —$SO_2NR^4R^5$, lower alkyl, cycloalkyl, aryl, and heteroaryl, wherein the lower alkyl and cycloalkyl each may be optionally substituted by the group $R^{11}$ and the aryl and heteroaryl each may be optionally substituted by the group $R^{12}$,
aryl which optionally may be substituted by the group consisting of —$OR^3$, —$NR^4R^5$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^3$, —$NR^4R^5$, halogen, —$NO_2$, perfluoroalkyl, —$COR^3$, —$COOR^3$, —$OCOR^3$, —$CONR^4R^5$, —CN, —$SO_2R^3$, —$SO_2NR^4R^5$, lower alkyl, cycloalkyl, heterocycle, aryl, and heteroaryl and wherein the lower alkyl, cycloalkyl and heterocycle each may be optionally substituted by the group $R^{11}$ and the aryl and heteroaryl each may be optionally substituted by the group $R^{12}$;

$R^2$ is selected from the group consisting of
—H,
—$OR^3$,
—$COR^3$,
—$COOR^3$,
—$OCOR^3$,
—$CONR^4R^5$,
halogen,
—CN,
perfluoroalkyl,
—$NR^4R^5$, and
lower alkyl which optionally may be substituted by the group consisting of —$OR^3$, —$OCOR^3$, and —$NR^4R^5$;

$R^3$ is selected from the group consisting of
—H,
lower alkyl which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^7$, —$COOR^6$, —$COR^6$, —$CONR^4R^5$, —$NR^4R^5$, —$SO_2R^6$, —$SO_2NR^4R^5$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$,
aryl which optionally may be substituted by the group consisting of —$OR^7$, —$COOR^6$, —$COR^6$, —$CONR^4R^5$, —$NR^4R^5$, —$NO_2$, halogen, perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^7$, —$COOR^6$, —$COR^6$, —$CONR^4R^5$, —$NR^4R^5$, —$NO_2$, halogen, perfluoroalkyl, —$SO_2R^6$, —$SO_2NR^4R^5$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^4$ and $R^5$ are each independently selected from the group consisting of
—H,
—$COR^6$,
—$COOR^6$,
—$CONR^6R^8$,
lower alkyl which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^7$, —$COOR^6$, —$COR^6$, —$CONR^6R^7$, —$NR^6$ $R^7$, —$SO_2R^6$, —$SO_2NR^6R^7$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^7$, —$COOR^6$, —$COR^6$, —$CONR^6R^7$, —$NR^6R^7$, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$,
aryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^7$, —$COOR^6$, —$COR^6$, —$CONR^6R^7$, —$NR^6R^7$, —$NO_2$, halogen, perfluoroalkyl, —$SO_2R^6$, —$SO_2NR^6R^7$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$; or
alternatively, —$NR^4R^5$ can optionally form a ring having 3 to 7 atoms, said ring optionally including one or more additional hetero atoms and being optionally substituted by the group consisting of lower alkyl, —$OR^7$, —$COR^6$, —$COOR^6$, —$CONR^6R^8$, and —$NR^7R^8$;
$R^6$ is selected from the group consisting of
—H, and
lower alkyl which optionally may be substituted by the group consisting of cycloalkyl, heterocycle, aryl, heteroaryl, —$OR^8$, and —$NR^7R^8$;
$R^7$ is selected from the group consisting of
—H,
—$COR^8$,
—$CONR^9R^8$, and
lower alkyl which optionally may be substituted by $R^{11}$;
$R^8$ and $R^9$ are each independently selected from the group consisting of —H and lower alkyl;

$R^{11}$ is selected from the group consisting of —$OR^8$, —$COR^8$, —$COOR^8$, —$OCOR^8$, —$CONR^8R^9$, —$NR^8R^9$, —$N(COR^8)R^9$, —$SO_2R^8$, and $SO_2NR^8R^9$;
$R^{12}$ is selected from the group consisting of —$OR^8$, —$COR^8$, —$COOR^8$, —$OCOR^8$, —$CONR^8R^9$, —$NR^8R^9$, —$N(COR^8)R^9$, —$SO_2R^8$, $SO_2NR^8R^9$, halogen, —CN, —$NO_2$, and perfluoroalkyl;
X is selected from the group consisting of

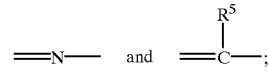

Y and Z are each independently selected from the group consisting of N, O, and S; provided that at least one of Y and Z is N and provided further that Y and Z are not both N; and
a is a double bond either between Y—C or Z—C.

2. The compound of claim 1 wherein $R^1$ is selected from the group consisting of
—H,
—$NR^4R$,
lower alkyl which optionally may be substituted by of —$OR^3$, —$COR^3$, —$COOR^3$, —$OCOR^3$, —$CONR^4R^5$, —$NR^4R^5$, —$SO_2R^3$, —$SO_2NR^4R^5$, cycloalkyl, heterocycle, aryl, and heteroaryl, and wherein the cycloalkyl and heterocycle optionally may be substituted by $R^{11}$ and the aryl and heteroaryl optionally may be substituted by $R^{12}$,
cycloalkyl which optionally may be substituted by $R^{11}$, lower alkyl, heterocycle, aryl, and heteroaryl, and wherein the lower alkyl and heterocycle optionally may be substituted by $R^{11}$ and the aryl and heteroaryl optionally may be substituted by $R^{12}$,
heterocycle which optionally may be substituted by $R^{11}$, lower alkyl, cycloalkyl, aryl, and heteroaryl, and wherein the lower alkyl and cycloalkyl optionally may be substituted by $R^{11}$ and the aryl and heteroaryl optionally may be substituted by $R^{12}$,
aryl which optionally may be substituted by $R^{12}$, lower alkyl, cycloalkyl, heterocycle, aryl, and heteroaryl, and wherein the lower alkyl, cycloalkyl and heterocycle, optionally may be substituted by $R^{11}$ and the heterocycle and heteroaryl optionally may be substituted by $R^{12}$, and
heteroaryl which optionally may be substituted by $R^{12}$, lower alkyl, cycloalkyl, heterocycle, and aryl, and wherein the lower alkyl and cycloalkyl optionally may be substituted by $R^{11}$ and the heterocycle and aryl optionally may be substituted by $R^{12}$.

3. The compound of claim 2 wherein $R^2$ is selected from the group consisting of
—H,
—$OR^3$,
—$NR^4R^5$, and
lower alkyl which optionally may be substituted by the group consisting of —$OR^3$ and —$NR^4R^5$.

4. The compound of claim 2 wherein $R^1$ is selected from the group consisting of
—H,
—$NR^4R^5$,
lower alkyl which optionally may be substituted by —$OR^3$, —$COR^3$, —$COOR^3$, —$OCOR^3$, —$CONR^4R^5$, —$NR^4R^5$, —$SO_2R^3$, —$SO_2NR^4R^5$, heterocycle, aryl and heteroaryl, wherein the heterocycle may be optionally substituted by $R^{11}$, and the aryl and heteroaryl optionally may be substituted by $R^{12}$, aryl which optionally may be substituted by $R^{12}$ and lower alkyl wherein the lower alkyl optionally may be further substituted by $R^{11}$; and heteroaryl which optionally may be substituted by $R^{12}$ and lower alkyl, wherein lower alkyl optionally may be further substituted by $R^{11}$.

5. The compound of claim 4 wherein $R^2$ is selected from the group consisting of

—H,

—$OR^3$, and lower alkyl which optionally may be substituted by the group consisting of —$OR^3$ and —$NR^4R^5$.

6. A compound selected from the group consisting of:

8-(3-Methoxy-1H-pyrrol-2-ylmethylene)-2-phenyl-6,8-dihydroxo-oxazolo[4,5-e]indol-7-one (E), 8-(3-Methoxy-1H-pyrrol-2-ylmethylene)-2-phenyl-6,8-dihydroxo-thiazolo[4,5-e]indol-7-one (F), 8-(3-Methoxy-1H-pyrrol-2-ylmethylene)-2-phenyl-6,8-dihydroxo-oxazolo[5,4-e]indol-7-one (G), and 8-(3-Methoxy-1H-pyrrol-2-ylmethylene)-2-phenyl-6,8-dihydroxo-thiazolo[5,4-e]indol-7-one (H).

7. A pharmaceutical composition comprising as an active ingredient an effective amount of a compound of claim 1 and a pharmaceutically acceptable carrier or excipient.

8. A pharmaceutical composition comprising as an active ingredient an effective amount of a compound of claim 2 and a pharmaceutically acceptable carrier or excipient.

9. A pharmaceutical composition comprising as an active ingredient an effective amount of a compound of claim 3 and a pharmaceutically acceptable carrier or excipient.

10. A pharmaceutical composition comprising as an active ingredient an effective amount of a compound of claim 4 and a pharmaceutically acceptable carrier or excipient.

11. A pharmaceutical composition comprising as an active ingredient an effective amount of a compound of claim 5 and a pharmaceutically acceptable carrier or excipient.

12. A pharmaceutical composition comprising as an active ingredient an effective amount of a compound of claim 6 and a pharmaceutically acceptable carrier or excipient.

13. The pharmaceutical composition of claim 12 which is suitable for parenteral administration.

14. A method for treating a cell proliferative disorder comprising administering to a subject in need thereof a therapeutically effective amount of a compound according to claim 1.

15. The method of claim 14 wherein the cell proliferative disorder is cancer.

16. The method of claim 15 wherein the cancer is a solid tumor.

17. The method of claim 16 wherein the solid tumor is a breast or colon tumor.

\* \* \* \* \*

UNITED STATES PATENT AND TRADEMARK OFFICE
CERTIFICATE OF CORRECTION

PATENT NO.    : 6,197,804
DATED         : March 6, 2001
INVENTOR(S)   : Kin-Chun Luk, Steven Gregory Mischke It is certified that error appears in the above-identified patent and that said Letters Patent is hereby corrected as shown below:

IN THE CLAIMS:

Claim 2, Column 58, line 24: "$NR^4R$," should read -- $NR^4R^5$, --.

Signed and Sealed this

Fifth Day of June, 2001

*Attest:*

*Attesting Officer*

NICHOLAS P. GODICI

*Acting Director of the United States Patent and Trademark Office*